US006440684B1

(12) United States Patent
Beraud et al.

(10) Patent No.: US 6,440,684 B1
(45) Date of Patent: Aug. 27, 2002

(54) METHODS OF IDENTIFYING MODULATORS OF KINESIN MOTOR PROTEINS

(75) Inventors: Christophe Beraud, San Francisco; Jeffrey T. Finer, Foster City; Roman Sakowicz, Foster City; Kenneth W. Wood, Foster City, all of CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/592,054

(22) Filed: Jun. 12, 2000

(51) Int. Cl.[7] .............................. C12N 9/16; C12Q 1/42
(52) U.S. Cl. ......................................... 435/19; 435/196
(58) Field of Search .................................. 435/196, 19

(56) References Cited

U.S. PATENT DOCUMENTS 6,207,403 B1 * 3/2001 Goldstein et al. ............. 435/21

OTHER PUBLICATIONS

Oh et al. GenBank Accession No. AF071592, Mar. 2000.*
Kim et al. GenBank Accession No. AF241316, Apr. 2000.*
Aizawa et al. (1992) "Kinesin family in murine central nervous system" J Cell Biol 119:1287–96.
Kim et al. (1998) "Binding of murine leukemia virus Gag polyproteins to KIF4, a microtubule–based motor protein" J Virol 72:6898–901.
Oh et al. (1998) Genbank Accession #U18309.1. Direct Submission.
Sekine et al. (1994) Genbank Accession #D12646. Direct Submission.
Powers et al. (1999) A C. elegans Chromokinesin Required for Chromosome Segregation) Molec. Biol. Cell 10:371a.
Sekine et al. (1994) "A novel microtubule–based motor protein (KIF4) for organelle transports, whose expression is regulated developmentally" J Cell Biol 127:187–201.
Vernos et al. (1996) "Motors involved in spindle assembly and chromosome segregation" Curr Opin Cell Biol 8:4–9.
Vernos et al. (1995) "Xklp1, a chromosomal Xenopus kinesin–like protein essential for spindle organization and chromosome positioning" Cell 81:117–27.
Wang et al. (1995) "Chromokinesin: a DNA–binding, kinesin–like nuclear protein" J Cell Biol 128:761–8.
Wang et al. (1994) "A Developmentally regulated basic–leucine zipper–like gene and its expression in embryonic retina and lens" Proc Natl Acad Sci U S A 91:1351–5.
Williams et al. (1995) "The Drosophila kinesin–like protein KLP3A is a midbody component required for central spindle assembly and initiation of cytokinesis" J Cell Biol 129:709–23.
Villard,L (1999) "Homo sapiens KIF4 (KIF4) mRNA, complete cDNA sequence" Genback Accession No. AF179308.
Tang et al. (1999) "Cellular motor protein Kif–4 associates with retroviral Gag" J. of Virology 10508–10513.

\* cited by examiner

*Primary Examiner*—Rebecca E. Prouty
*Assistant Examiner*—David Steadman
(74) *Attorney, Agent, or Firm*—Lauren L. Stevens, Esq.; Beyer Weaver & Thomas, LLP

(57) ABSTRACT

The present invention provides high throughput screening systems for identifying compounds useful in the treatment of cellular proliferation disorders. The method can be performed in plurality simultaneously with fluorescence or absorbance readouts.

21 Claims, 9 Drawing Sheets

FIG. 1

```
gggaggccca gggagaacgg ggaagggaca tttagtttga gacggtgctg agataggatc 61
ATGaaggaag aggtgaaggg aattcctgta agagtggcgc tgcgttgtcg ccctctggtc 121
cccaaagaga ttagcgaggg ctgccagatg tgcctttcct tcgtgcccgg agagcctcag 181
gtggtggttg gtacagataa atccttcacc tacgattttg tatttgatcc ctctactgaa 241
caggaagaag tcttcaatac agcagtagcg ccactcataa aaggtgtatt taaaggatat 301
aatgcaacgg tcctggccta tgggcagact ggctctggaa aaacctattc aatgggaggt 361
gcatatactg cagagcaaga gaatgaacca acagttgggg ttattcctag ggtaatacaa 421
ctgctcttca aagaaattga taaaaagagt gactttgaat ttactctgaa agtgtcttac 481
ttagagattt acaatgaaga aattttggat cttctatgtc catctcgtga gaaagctcaa 541
ttagagattt acaatgaaga aattttggat cttctatgtc catctcgtga gaaagctcaa 601
gttttggttg ccttggatac tgtttcctgt ttggaacagg gcaacaactc taggactgtg 661
gcctccacgg ctatgaactc ccagtcgtcc cgatctcatg ccatcttaac aatctcctta 721
gagcaaggaa agaaaagtga caagaatagc agctttcgct ccaagctgca tcttgtagac 781
ctcgctggat cagaaagaca gaagaaaacc aaggctgaag gggatcgtct aaaagagggt 841
attaatatta accgaggcct cctatgcttg ggaaatgtaa tcagtgctct tggagatgac 901
aaaaagggtg gctttgcgcc ctacagagat tccaagttga ctcgactgct tcaagattct 961
ctaggaggta atagccatac tcttatgata gcctgtgtga gtcctgctga ctccaatcta 1021
gaggaaacat taaatacccct tcgctatgct gacagagcaa gaaaaatcaa gaacaaacct 1081
attgttaata ttgatcccca gacagctgaa cttaatcatc taaagcaaca ggtacaacag 1141
ctacaagtct tgttgctaca ggcccatgga ggtaccctgc ctggatctat aactgtggaa 1201
ccatcagaga atctacaatc cctgatggag aagaatcagt ccctggtaga ggagaatgaa 1261
aaattaagtc gtggtctgag cgaggcagct ggtcagacga cccagatgct ggagaggatc 1321
atttggacag agcaagcgaa tgaaaaaatg aacgccaagc tagaagagct caggcagcat 1381
gcggcctgca aactggatct tcaaaagcta gtggagactt tggaagacca ggaattgaaa 1441
gaaaatgtag agataattttg taacctgcag caattgatta cccagttatc ggatgaaact 1501
gttgcttgca tggctgcagc cattgatact gcggtggagc aagaagccca agtagaaacc 1561
agtccagaga cgagcaggtc ttctgacgct tttaccactc agcatgctct ccgtcaagcg 1621
cagatgtcta aggagctggt tgagttgaat aaagcgcttg cactgaaaga ggccctggct 1681
aggaagatga ctcagaatga cagccaactg cagcctattc agtaccaata ccaggataac 1741
ataaaagagc cagaattaga agtcatcaat ctgcaaaagg aaaaggaaga attggttctt 1801
gaacttcaga cagcaaagaa ggatgccaac caagccaagt tgagtgagcg ccgccgcaaa 1861
cgtctccagg agctggaggg tcaaattgct gatctgaaga agaaactgaa tgagcagtcc 1921
aaacttctga aactaaagga atccacagag cgtactgtct ccaaactgaa ccaggagata 1981
cggatgatga aaaaccagcg ggtacagtta atgcgtcaaa tgaaagaaga tgctgagaag 2041
tttagacagt ggaagcagaa aagagacaaa gaagtaatac agttaaaaga acgagaccgt 2101
aagaggcaat atgagctgct gaaacttgaa agaaacttcc agaaacaatc caatgtgctc 2161
agacgtaaaa cggaggaggc agcagctgcc aacaagcgtc tcaaggatgc tctccagaaa 2221
caacgggagg ttgcagataa gcggaaagag actcagagcc gtggaatgga aggcactgca 2281
gctcgagtga agaattggct tggaaacgaa attgaggtta tggtcagtac tgaggaagcc 2341
aaacgccatc tgaatgacct ccttgaagat agaaagatcc tggctcaaga tgtggctcaa 2401
ctcaaagaaa aaaaggaatc tggggagaat ccacctccta aactccggag gcgtacattc 2461
tcccttactg aagtgcgtgg tcaagtttcg gagtcagaag attctattac aaagcagatt 2521
gaaagcctag agactgaaat ggaattcagg agtgctcaga ttgctgacct acagcagaag 2581
ctgctggatg cagaaagtga agacagacca aaacaacgct gggagaatat tgccaccatt 2641
ctggaagcca agtgtgccct gaaatatttg attggagagc tggtctcctc caaaatacag 2701
gtcagcaaac ttgaagcag cctgaaacag gctgtgctga catgcgagag 2761
atgctgtttg aggaacgaaa tcattttgcc gagatagaga cagagttaca agctgagctg 2821
gtcagaatgg agcaacagca cccagagaag gtgctgtacc ttctcagcca gctgcagcaa 2881
agccaaatgg cagagaagca gttagaggaa tcagtcagtg aaaaggaaca gcagctgcaa 2941
agcacactga agtgtcagga tgaagaactt gagaaaatgc gagaagtgtg tgagcaaaat 3001
cagcagcttc tccgagagaa tgaaatcatc aagcagaaac tgaccctcct ccaggtagcc 3061
agcagcagaa aacatcttcc taaggatacc ctttcatctc cagactcttc ttttgaatat 3121
gtccagccta agccaaaacc ttctcgtgtt aaagaaaagt tcctggagca aagcatggac 3181
atcgaggatc taaaatattg ttcagagcat tctgtgaatg agcatgagga tggtgatggt 3241
gatgatgatg aggggatga cgaggaatga aagccaacaa aattagttaa tgtgtccagg 3301
aagaacatcc aagggtgttc ctgcaagggc tggtgtggaa acaagcaatg tgggtgcagg 3361
aagcaaaagt cagactgtgg tgtggactgt tgctgtgacc ccacaaagtg tcggaaccgc 3421
cagcaggca aggatagctt gggcactgtt gaacggaccc aggattcaga aagctccttc 3481
aaactggagg atcctaccga ggtgacccca ggattgagct tctttaatcc cgtctgtgcc 3541
acccccaata gcaagatcct gaaagagatg tgcgatgtgg agcaggtgct gtcaaagaag 3601
actccccag ctccctcccc ttttgacctc ccagagttaa aacatgtagc aacagaatac 3661
caagaaaaca agggctccgg gaagaaaaag aaacgggctc tggccagcaa caccagcttc 3721
ttctctggct gctccctat cgaagaagag gcccacTGAa gttggagtca tcatctctac 3781
ccccagtctg gcttgggaga tgctttcagg ttgcagccag aagggttttt taatgactct 3841
ctgattcagt tcttgctgtt gaaaaggaac aagcgttact gaaaagaagg taaccttgtt 3901
tggatgtggg ccttagcctc caggtccaga ctactactgt atgttctcca gaagggtgct 3961
aagtcaccta cgaagagaga accaacagac tttcctattg actcatcagg aaccagtcct 4021
cagtctggtc aagttgtttc ttatttgtga gcagttcagg ccatctcctg atggggatga 4081
gcccaaggct ttcttatctt ttggtcgtct ccgcttaatg gaggagcctg gcctaggatg 4141
gaggcctggc ttagatcttt cattccacct caagaatgag gttgtgatct ttcctgtcct 4201
gaccctctct gaattatgtt tcaatagtac tcttgattgt ctgccatgtt gttgaagcaa 4261
atgaattatt tttaaatgtt aagtaagtaa ataaaccttta gcccgtct (SEQ ID NO:1)
```

FIG. 2

MKEEVKGIPVRVALRCRPLVPKEISEGCQMCLSFVPGEPQVVVG
TDKSFTYDFVFDPSTEQEEVFNTAVAPLIKGVFKYNATVLAYGQTGSGKTYSMGGA
YTAEQENEPTVGVIPRVIQLLFKEIDKKSDFEFTLKVSYLEIYNEEILDLLCPSREK
AQINIREDPKEGIKIVGLTEKTVLVALDTVSCLEQGNNSRTVASTAMNSQSSRSHAI
LTISLEQGKKSDKNSSFRSKLHLVDLAGSERQKKTKAEGDRLKEGININRGLLCLGN
VISALGDDKKGGFAPYRDSKLTRLLQDSLGGNSHTLMIACVSPADSNLEETLNTLRY
ADRARKIKNKPIVNIDPQTAELNHLKQQVQQLQVLLLQAHGGTLPGSITVEPSENLQ
SLMEKNQSLVEENEKLSRGLSEAAGQTAQMLERIIWTEQANEKMNAKLEELRQHAAC
KLDLQKLVETLEDQELKENVEIICNLQQLITQLSDETVACMAAAIDTAVEQEAQVET
SPETSRSSDAFTTQHALRQAQMSKELVELNKALALKEALARKMTQNDSQLQPIQYQY
QDNIKEPELEVINLQKEKEELVLELQTAKKDANQAKLSERRRKRLQELEGQIADLKK
KLNEQSKLLKLKESTERTVSKLNQEIRMMKNQRVQLMRQMKEDAEKFRQWKQKRDKE
VIQLKERDRKRQYELLKLERNFQKQSNVLRRKTEEAAAANKRLKDALQKQREVADKR
KETQSRGMEGTAARVKNWLGNEIEVMVSTEEAKRHLNDLLEDRKILAQDVAQLKEKK
ESGENPPPKLRRRTFSLTEVRGQVSESEDSITKQIESLETEMEFRSAQIADLQQKLL
DAESEDRPKQRWENIATILEAKCALKYLIGELVSSKIQVSKLESSLKQSKTSCADMQ
KMLFEERNHFAEIETELQAELVRMEQQHPEKVLYLLSQLQQSQMAEKQLEESVSEKE
QQLQSTLKCQDEELEKMREVCEQNQQLLRENEIIKQKLTLLQVASRQKHLPKDTLLS
PDSSFEYVQPKPKPSRVKEKFLEQSMDIEDLKYCSEHSVNEHEDGDGDDDEGDDEEW
KPTKLVNVSRKNIQGCSCKGWCGNKQCGCRKQKSDCGVDCCCDPTKCRNRQQGKDSL
GTVERTQDSESSFKLEDPTEVTPGLSFFNPVCATPNSKILKEMCDVEQVLSKKTPPA
PSPFDLPELKHVATEYQENKGSGKKKKRALASNTSFFSGCSPIEEEAH (SEQ ID
NO:2)

FIG. 3

```
1    atggctagca tgactggtgg acagcaaatg ggtcggatcc gaattcgagc
51   tccgtcgaca agcttggaag aggtgaaggg aattcctgta agagtggcgc
101  tgcgttgtcg ccctctggtc cccaaagaga ttagcgaggg ctgccagatg
151  tgcctttcct tcgtgcccgg agagcctcag gtggtggttg gtacagataa
201  atccttcacc tacgattttg tatttgatcc ctctactgaa caggaagaag
251  tcttcaatac agcagtagcg ccactcataa aaggtgtatt taaggatat
301  aatgcaacgg tcctggccta tgggcagact ggctctggaa aaacctattc
351  aatgggaggt gcatatactg cagagcaaga gaatgaacca acagttgggg
401  ttattcctag ggtaatacaa ctgctcttca aagaaattga taaaaagagt
451  gactttgaat ttactctgaa agtgtcttac ttagagattt acaatgaaga
501  aattttggat cttctatgcc catctcgtga gaaagctcaa ataaatatac
551  gagaggatcc taaggaaggc ataaagattg tgggactcac tgagaagact
601  gttttggttg ccttggatac tgtttcctgt ttggaacagg caacaactc
651  taggactgtg gcctccacgg ctatgaactc ccagtcgtcc cgatctcatg
701  ccatctttac aatctcctta gagcaaagaa agaaaagtga caagaatagc
751  agctttcgct ccaagctgca tcttgtagac ctcgctggat cagaaagaca
801  gaagaaaacc aaggctgaag gggatcgtct aaaagagggt attaatatta
851  accgaggcct cctatgcttg ggaaatgtaa tcagtgctct ggagatgac
901  aaaaagggtg gctttgtgcc ctacagagat tccaagttga ctcgactgct
951  tcaagattct ctaggaggta atagccatac tcttatgata gcctgtgtga
1001 gtcctgctga ctccaatcta gaggaaacat taaatacccct tcgctatgct
1051 gacagagcaa gaaaaatcaa gaacaaacct attgttaata ttgatcccca
1101 gacagctgaa cttaatcatc taaagcaaca ggtacaacag ctacaagtct
1151 tgttgctaca ggcccatgga ggtaccctgc tggatctat aactgtggaa
1201 ccatcagaga atctacaatc cctgatggag aagaatcagt ccctggtaga
1251 ggagaatgaa aaattaagtc gtggtctgag cgaggcagct ggtcagacag
1301 cccagatgtt ggagaggatc atttggacag agcaagcgaa tgaaaaaatg
1351 aacgccaagc tagaagagct caggcagcat gcggcctgca aactggatct
1401 tcaaaagcta gtggagactt tggaagacca ggaattgaaa gaaatgtag
1451 agataatttg taacctgcag caattgatta cccagaagct tgcggccgca
1501 ctcgagggta ccgagcagaa gctgatcagc gaggaggacc tgatcgagca
1551 ccaccaccac caccactga   (SEQ ID NO:3)
```

FIG. 4

```
1    MASMTGGQQM GRIRIRAPST SLEEVKGIPV RVALRCRPLV PKEISEGCQM
51   CLSFVPGEPQ VVVGTDKSFT YDFVFDPSTE QEEVFNTAVA PLIKGVFKGY
101  NATVLAYGQT GSGKTYSMGG AYTAEQENEP TVGVIPRVIQ LLFKEIDKKS
151  DFEFTLKVSY LEIYNEEILD LLCPSREKAQ INIREDPKEG IKIVGLTEKT
201  VLVALDTVSC LEQGNNSRTV ASTAMNSQSS RSHAIFTISL EQRKKSDKNS
251  SFRSKLHLVD LAGSERQKKT KAEGDRLKEG ININRGLLCL GNVISALGDD
301  KKGGFVPYRD SKLTRLLQDS LGGNSHTLMI ACVSPADSNL EETLNTLRYA
351  DRARKIKNKP IVNIDPQTAE LNHLKQQVQQ LQVLLLQAHG GTLPGSITVE
401  PSENLQSLME KNQSLVEENE KLSRGLSEAA GQTAQMLERI IWTEQANEKM
451  NAKLEELRQH AACKLDLQKL VETLEDQELK ENVEIICNLQ QLITQKLAAA
501  LEGTEQKLIS EEDLIEHHHH HH*  (SEQ ID NO:4)
```

FIG. 5

```
    tggaag aggtgaaggg aattcctgta agagtggcgc tgcgttgtcg
ccctctggtc cccaaagaga ttagcgaggg ctgccagatg tgcctttcct
tcgtgcccgg agagcctcag gtggtggttg gtacagataa atccttcacc
tacgattttg tatttgatcc ctctactgaa caggaagaag tcttcaatac
agcagtagcg ccactcataa aaggtgtatt taaaggatat aatgcaacgg
tcctggccta tgggcagact ggctctggaa aaacctattc aatgggaggt
gcatatactg cagagcaaga gaatgaacca acagttgggg ttattcctag
ggtaatacaa ctgctcttca aagaaattga taaaagagt gactttgaat
ttactctgaa agtgtcttac ttagagattt acaatgaaga aattttggat
cttctatgcc catctcgtga gaaagctcaa ataaatatac gagaggatcc
taaggaaggc ataaagattg tgggactcac tgagaagact gttttggttg
ccttggatac tgtttcctgt ttggaacagg caacaactc taggactgtg
gcctccacgg ctatgaactc ccagtcgtcc cgatctcatg ccatctttac
aatctcctta gagcaaagaa agaaaagtga caagaatagc agctttcgct
ccaagctgca tcttgtagac ctcgctggat cagaaagaca gaagaaaacc
aaggctgaag gggatcgtct aaaagagggt attaatatta accgaggcct
cctatgcttg ggaaatgtaa tcagtgctct tggagatgac aaaaagggtg
gctttgtgcc ctacagagat tccaagttga ctcgactgct tcaagattct
ctaggaggta atagccatac tcttatgata gcctgtgtga gtcctgctga
ctccaatcta gaggaaacat taaataccct tcgctatgct gacagagcaa
gaaaaatcaa gaacaaacct attgttaata ttgatcccca gacagctgaa
cttaatcatc taaagcaaca ggtacaacag ctacaagtct tgttgctaca
ggcccatgga ggtaccctgc ctggatctat aactgtggaa ccatcagaga
atctacaatc cctgatggag aagaatcagt ccctggtaga ggagaatgaa
aaattaagtc gtggtctgag cgaggcagct ggtcagacag cccagatgtt
ggagaggatc atttggacag agcaagcgaa tgaaaaaatg aacgccaagc
tagaagagct caggcagcat gcggcctgca aactggatct tcaaaagcta
gtggagactt tggaagacca ggaattgaaa gaaaatgtag agataatttg
taacctgcag caattgatta cccag (SEQ ID NO:5)
```

FIG. 6

```
    EEVKGIPV  RVALRCRPLV  PKEISEGCQM  CLSFVPGEPQ  VVVGTDKSFT
YDFVFDPSTE  QEEVFNTAVA  PLIKGVFKGY  NATVLAYGQT  GSGKTYSMGG
AYTAEQENEP  TVGVIPRVIQ  LLFKEIDKKS  DFEFTLKVSY  LEIYNEEILD
LLCPSREKAQ  INIREDPKEG  IKIVGLTEKT  VLVALDTVSC  LEQGNNSRTV
ASTAMNSQSS  RSHAIFTISL  EQRKKSDKNS  SFRSKLHLVD  LAGSERQKKT
KAEGDRLKEG  ININRGLLCL  GNVISALGDD  KKGGFVPYRD  SKLTRLLQDS
LGGNSHTLMI  ACVSPADSNL  EETLNTLRYA  DRARKIKNKP  IVNIDPQTAE
LNHLKQQVQQ  LQVLLLQAHG  GTLPGSITVE  PSENLQSLME  KNQSLVEENE
KLSRGLSEAA  GQTAQMLERI  IWTEQANEKM  NAKLEELRQH  AACKLDLQKL
VETLEDQELK  ENVEIICNLQ  QLITQ  (SEQ ID NO:6)
```

FIG. 7A

```
   1  TTTGAAACTT GGCGGTTAAA GCTCCGGCTG GGCAGGGGCG GCGGGAGACC
  51  CCGGGTGAAC GGGGAAGGGA CATTTAGTTT GAGACGGTGC TGAGATAGGA
 101  TCATGAAGGA AGAGGTGAAG GGAATTCCTG TAAGAGTGGC ACTGCGTTGT
 151  CGCCCTCTGG TCCCCAAAGA GATTAGCGAG GGCTGCCAGA TGTGCCTTTC
 201  CTTCGTGCCC GGGGAGACTC AGGTGGTGGT TGGTACTGAT AAATCCTTCA
 251  CCTACGATTT TGTGTTTGAC CCCTGTACTG AGCAGGAAGA AGTCTTCAAT
 301  AAAGCAGTAG CGCCGCTCAT AAAAGGCATA TTTAAAGGAT ATAATGCAAC
 351  GGTCCTGGCC TATGGGCAGA CTGGCTCTGG AAAAACCTAT TCAATGGGAG
 401  GTGCATACAC TGCGGAGCAG GAGAATGAAC CAACAGTTGG CATTATTCCT
 451  AGGGTAATAC AACTGCTCTT CAAAGAAATT GATCAAAGA GTGACTTTGA
 501  ATTTACTCTG AAAGTGTCTT ACTTAGAGAT TTACAATGAA GAAATTTTGG
 551  ATCTTCTATG CCCATCTCGT GAGAAAGCTC AAATAAATAT ACGGGAGGAT
 601  CCTAAGGAAG GCATAAAGAT TGTGGGACTC ACTGAGAAGA CTGTTTTAGT
 651  TGCCTTGGAT ACTGTTTCCT GTTTGGAGCA GGGCAACAAC TCTAGGACTG
 701  TGGCCTCCAC AGCTATGAAC TCCCAGTCGT CCCGATCTCA TGCCATCTTT
 751  ACAATCTCCT TAGAGCAAGG AAAGAAAAGT GACAAGAATA GCAGCTTTCG
 801  CTCCAAGCTG CATCTTGTAG ACCTCGCTGG ATCAGAAAGA CAGAAGAAAA
 851  CCAAGGCTGA AGGGGATCGT CTAAAAGAGG GTATTAATAT TAACCGAGGC
 901  CTCCTATGCT TGGGAAATGT AATCAGTGCT CTTGGAGATG ACAAAAAGGG
 951  TAGCTTTGTG CCCTACAGAG ATTCCAAGTT AACTCGACTG CTGCAAGATT
1001  CTCTAGGAGG TAACAGCCAC ACTCTTATGA TAGCCTGTGT GAGTCCTGCT
1051  GACTCCAATC TAGAGGAAAC ATTAAGTACC CTTCGCTATG CTGACAGAGC
1101  AAGAAAAATC AAGAACAAAC CTATTGTTAA TATTGATCCC CACACAGCTG
1151  AACTTAATCA TCTAAAGCAA CAGGTACAAC AGCTACAAGT CTTGTTGCTA
1201  CAAGCCCATG GAGGTACCCT GCCTGGATCT ATAAATGCAG AACCATCAGA
1251  GAATCTACAA TCCCTGATGG AGAAGAATCA GTCCCTGGTA GAGGAGAATG
1301  AAAAATTAAG TCGTTGTCTG AGCAAGGCAG CTGGTCAGAC AGCCCAGATG
1351  TTGGAGAGGA TCATTTTGAC AGAGCAAGTG AATGAAAAAC TGAACGCCAA
1401  GCTAGAAGAG CTCAGGCAGC ATGCGGCCTG CAAGCTGGAT CTTCAAAAGC
1451  TAGTGGAGAC TTTGGAAGAC CAGGAATTGA AAGAAAATGT AGAGATAATT
1501  TGTAACCTGC AGCAACTGAT TACCCAGTTA TCAGATGAAA CTGTTGCTTG
1551  CACGGCTGCA GCCATTGATA CTGCGGTAGA AGAAGAAGCT CAAGTGGAAA
1601  CCAGTCCAGA GACAAGCAGG TCTTCTGACG CTTTTACCAC TCAGCATGCT
1651  CTCCATCAAG CTCAGATGTC TAAGGAGGTG GTTGAGTTGA ATAACGCCCT
1701  TGCACTGAAA GAGGCCCTAG TTAGGAAGAT GACTCAGAAC GACAACCAAC
1751  TACAGCCCAT TCAGTTTCAA TACCAGGATA ACATAAAAAA TCTAGAATTA
1801  GAAGTCATCA ATCTGCAAAA GGAAAAGGAA GAATTGGTTC GTGAACTTCA
1851  GACAGCAAAG AAGAATGCCA ACCAAGCCAA GCTGAGTGAG CACCGTCGCA
1901  AACTTCTCCA GGAGCTGGAG GGTCAAATAG CTGATCTGAA GAAGAAACTG
1951  AATGAGCAGT CCAAACTTCT GAAACTAAAG GAATCCACAG AGCGTACTGT
2001  CTCCAAACTG AACCAGGAGA TACGGATGAT GAAAAACCAG CGGGTACAGT
2051  TAATGCGTCA AATGAAAGAG GATGCTGAGA AGTTTAGACA GTGGAAGCAG
2101  AAAAGAGACA AGAAGTAAT ACAGTTAAAA GAACGAGACC GTAAGAGGCA
2151  ATATGAGCTG CTGAAACTTG AAAGAAACTT CCAGAAACAA TCCAATGTGC
2201  TCAGACGTAA AACGGAGGAG GCAGCAGCTG CCAACAAGCG TCTCAAGGAT
2251  GCTCTCCAGA ACAACGGGA GGTTGCAGAT AAGCGGAAAG AGACTCAGAG
2301  CCGTGGAATG GAAGGCACTG CAGCTCGAGT GAGGAATTGG CTTGGAAATG
2351  AAATTGAGGT TATGGTCAGT ACTGAGGAAG CCAAACGCCA TCTGAATGAC
2401  CTCCTTGAAG ACAGAAAGAT CCTGGCTCAG GATGTGGTTC AACTCAAAGA
2451  AAAAAAGGAA TCTCGGGAGA ATCCACCTCC TAAACTCCGG AAGTGTACAT
2501  TCTCCCTTTC TGAGGTGCAT GGTCAAGTTT GGAGTCAGA AGATTGTATT
2551  ACAAAACAGA TTGAAAGCCT AGAGACTGAA ATGGAACTCA GGAGTGCTCA
2601  GATTGCTGAC CTACAGCAGA AGCTGCTGGA TGCAGAAAGT GAAGATAGGC
```

Fig. 7B

```
2651  CAAAACAATG CTGGGAGAAT ATTGCCACCA TTCTGGAAGC CAAGTGTGCC
2701  CTGAAATATT TGATTGGAGA GCTGGTCTCC TCCAAAATAC ATGTCACCAA
2751  ACTTGAAAAC AGCCTGAGAC AGAGCAAGGC CAGCTGTGCT GACATGCAGA
2801  AGATGCTATT TGAGGAACAA AATCATTTTT CTGAGATAGA GACAGAGTTA
2851  CAAGCTGAGC TGGTCAGAAT GGAGCAACAG CACCAAGAGA AGGTGCTATA
2901  CCTTGTCAGC CAGCTGCAGG AAAGCCAAAT GGCAGAGAAG CAGTTAGAGA
2951  AATCAGCCAG TGAAAAGGAA CCACAGTTGG TGAGCACACT GCAGTGTCAG
3001  GATGAAGAAC TTGAGAAGAT GCGAGAAGTG TGTGAGCAAA ATCAGCAGCT
3051  TCTCCAAGAG AATGAAATCA TCAAGCAGAA ACTGATCCTC CTCCAGGTAG
3101  CCAGCAGACA GAAACATCTT CCTAATGATA CCCTTCTATC TCCAGACTCT
3151  TCTTTTGAAT ATATCCCACC TAAGCCAAAA CCTTCTCGTG TTAAAGAAAA
3201  GTTTCTGGAG CAAAGCATGG ACATCGAGGA TCTAAAATAT TGTTCAGAGC
3251  ATTCTGTGAA TGAGCATGAA GATGGTGATG GTGATGGCGA CAGTGATGAG
3301  GGGGATGATG AGGAATGGAA GCCAACAAAA TTAGTCAAGG TGTCCAGGAA
3351  GAACATCCAA GGGTGTTCCT GCAAGGGCTG GTGTGGGAAC AAGCAGTGTG
3401  GGTGCAGGAA GCAAAGTCA GACTGTGGTG TGGACTGTAG CTGTGACCCC
3451  ACAAAGTGTC GGAACCGCCA GCAAGGCAAG GATAGCTTGG GCACTGTTGA
3501  ACAGACCCAG GATTCCGAAG CTCCTTCAA ACTGGAGGAT CCTACCGAGG
3551  TGACCCCAGG ATTGAGCTTC TTTAACCCTG TCTGTGCCAC CCCCAATAGC
3601  AAGATCCTGA AAGAGATGTG TGACATGGAG CAGGTGCTGT CAAAGAAGAC
3651  TGCTCCAGCT CCCTCCCCTT TTGACCTCCC AGAGTCGAAA CATGGAGCAA
3701  CAGAATACCA ACAAAATAAG CCTCCAGGGA AGAAAAAGAA ACGAGCTCTG
3751  GCTAGCAACA CCAGCTTCTT CTCTGGCTGC TCCCCTATTG AAGAAGAGGC
3801  CCACTGAAGT GGAGTCATC ATCTCTACCC CCAATCTGGC TTGGGAGATG
3851  CTTTCCAGTT GCAGCCAGAA GGGGTTTTTT AAATGACTTC TCTGGATTTC
3901  AGGTTTCTTG CCGTTGAAAA AAAGGAACAA AGCATTACTA AAAAGAAGGT
3951  AACCTTTGTT GGATGTTGTC CCTCAGTCTC CATCCCCAGA CTACTGCTCT
4001  CTGCTCTCTA GAAGGCTGCT AAACCACCTG CTGAAGAGAG AACCAACAGA
4051  CTTTCCTAAT GACTACTCAG GAACCAGTCC TCAGTATGAT CAAGTTCCTT
4101  CTTATTTGTG AGCAGTTCAG GCTAT  (SEQ ID NO:7)
```

FIG. 8

```
   1  MKEEVKGIPV  RVALRCRPLV  PKEISEGCQM  CLSFVPGETQ  VVVGTDKSFT
  51  YDFVFDPCTE  QEEVFNKAVA  PLIKGIFKGY  NATVLAYGQT  GSGKTYSMGG
 101  AYTAEQENEP  TVGIIPRVIQ  LLFKEIDQKS  DFEFTLKVSY  LEIYNEEILD
 151  LLCPSREKAQ  INIREDPKEG  IKIVGLTEKT  VLVALDTVSC  LEQGNNSRTV
 201  ASTAMNSQSS  RSHAIFTISL  EQGKKSDKNS  SFRSKLHLVD  LAGSERQKKT
 251  KAEGDRLKEG  ININRGLLCL  GNVISALGDD  KKGSFVPYRD  SKLTRLLQDS
 301  LGGNSHTLMI  ACVSPADSNL  EETLSTLRYA  DRARKIKNKP  IVNIDPHTAE
 351  LNHLKQQVQQ  LQVLLLQAHG  GTLPGSINAE  PSENLQSLME  KNQSLVEENE
 401  KLSRCLSKAA  GQTAQMLERI  ILTEQVNEKL  NAKLEELRQH  AACKLDLQKL
 451  VETLEDQELK  ENVEIICNLQ  QLITQLSDET  VACTAAAIDT  AVEEEAQVET
 501  SPETSRSSDA  FTTQHALHQA  QMSKEVVELN  NALALKEALV  RKMTQNDNQL
 551  QPIQFQYQDN  IKNLELEVIN  LQKEKEELVR  ELQTAKKNAN  QAKLSEHRRK
 601  LLQELEGQIA  DLKKKLNEQS  KLLKLKESTE  RTVSKLNQEI  RMMKNQRVQL
 651  MRQMKEDAEK  FRQWKQKRDK  EVIQLKERDR  KRQYELLKLE  RNFQKQSNVL
 701  RRKTEEAAAA  NKRLKDALQK  QREVADKRKE  TQSRGMEGTA  ARVRNWLGNE
 751  IEVMVSTEEA  KRHLNDLLED  RKILAQDVVQ  LKEKKESREN  PPPKLRKCTF
 801  SLSEVHGQVL  ESEDCITKQI  ESLETEMELR  SAQIADLQQK  LLDAESEDRP
 851  KQCWENIATI  LEAKCALKYL  IGELVSSKIH  VTKLENSLRQ  SKASCADMQK
 901  MLFEEQNHFS  EIETELQAEL  VRMEQQHQEK  VLYLVSQLQE  SQMAEKQLEK
 951  SASEKEPQLV  STLQCQDEEL  EKMREVCEQN  QQLLQENEII  KQKLILLQVA
1001  SRQKHLPNDT  LLSPDSSFEY  IPPKPKPSRV  KEKFLEQSMD  IEDLKYCSEH
1051  SVNEHEDGDG  DGDSDEGDDE  EWKPTKLVKV  SRKNIQGCSC  KGWCGNKQCG
1101  CRKQKSDCGV  DCSCDPTKCR  NRQQGKDSLG  TVEQTQDSEG  SFKLEDPTEV
1151  TPGLSFFNPV  CATPNSKILK  EMCDMEQVLS  KKTAPAPSPF  DLPESKHGAT
1201  EYQQNKPPGK  KKKRALASNT  SFFSGCSPIE  EEAH       (SEQ ID NO:8)
```

METHODS OF IDENTIFYING MODULATORS OF KINESIN MOTOR PROTEINS

FIELD OF THE INVENTION

The invention relates to methods for the identification of compounds that modulate the activity of target proteins having motor domains and use of such methods for the identification of therapeutic agents.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules (from the minus to the plus end of the microtubule, hence it is a "plus-end directed" motor).

KIF (KInesin Family) proteins are microtubule-dependent molecular motors that play important roles in intracellular transport and cell division. More specifically, several of these kinesins have been found associated with the arms of mitotic chromosomes. These kinesins are thought to provide a force, sometimes referred to as the polar ejection force, that is directed away from each spindle pole and is thought to contribute to movement of mitotic chromosomes toward the mitotic spindle midzone during prometaphase of mitosis. These kinesins are sometimes collectively referred to as chromokinesins.

Within this functional group of kinesins resides a group of kinesins from several organisms that share significant sequence homology. These include human Kif4 (HsKif4), murine Kif4 (MmKif4), and Xenopus laevis XKlp1, which are all closely related and are probably functional orthologs. Drosophila nod, and Drosophila Klp3A and C. elegans ChromoK-A and -B are more distantly related, but also appear to function during mitosis.

No studies of human Kif4 have been reported in the literature. cDNA sequence spanning the coding region of the HsKif4 RNA is entered under two Genbank accesssion numbers, AF071592 and AF179308.

A full length version of Kif4b, the Chromosome 5 Kif4 variant, has been identified. The two proteins are 93.9% identical overall, 97.1% in the motor domain. The DNA sequences share 95% identity in a 3845 bp overlap which includes some non-coding sequence.

The murine kinesin MmKif4 was identified in a PCR-based search for novel kinesins in the mouse nervous system, and appears as full length sequence in Genbank under the Accession number NM_008446. This gene is expressed in several tissues during early development, but is largely absent from adult tissues, with the exception of the spleen. Full length cloning of the MmKif4 cDNA; expression of full length MmKif4 in insect cells using a baculovirus expression vector; measurement of microtubule-stimulated ATPase of MmKif4; and analysis of MmKif4 microtubule binding and gliding activities have also been reported. MmKif4 has also been reported to interact with the murine leukemia virus Gag polyprotein.

XKlp1 is the Xenopus laevis ortholog of MmKif4. The full length sequence of XKlp1 has been reported. See, Accession number X82012. Xklp1 expression was found to be most prominent in gametes and dividing cells, and was localized to interphase nuclei, mitotic chromosomes, and to the spindle midzone. Perturbation of XKlp1 function by either antisense oligonucleotide injection into developing Xenopus embryos, or by antibody addition to mitotic spindle assembly reactions in vitro led to dramatic defects in mitotic spindle formation.

Chromokinesin was identified as an mRNA expressed in early embryonic neurons of the chicken. The initial cDNA clone did not include the motor domain, and chromokinesin was not identified as a kinesin until the remainder of the cDNA clone was identified. Chicken chromokinesin was found to be expressed preferentially, if not exclusively in proliferating cells of the developing chick retina, and was localized to the nuclei of interphase cells, and to chromosomes of mitotic cells.

Defects in function of these proteins would be expected to cause a failure in prometaphase chromosome alignment resulting in cell cycle arrest in mitosis. As such, compounds that modulate the activity of the chromokinesins may affect cellular proliferation. The present invention provides a novel method to identify such compounds.

SUMMARY OF THE INVENTION

The present invention provides methods to identify candidate agents that bind to a target protein or act as a modulator of the binding characteristics or biological activity of a target protein. In one embodiment, the method is performed in plurality simultaneously. For example, the method can be performed at the same time on multiple assay mixtures in a multi-well screening plate. Furthermore, in a preferred embodiment, fluorescence or absorbance readouts are utilized to determine activity. Thus, in one aspect, the invention provides a high throughput screening system for detecting modulators of activity a target protein.

In one embodiment, the present invention provides a method of identifying a candidate agent as a modulator of the activity of a target protein. The method comprises adding a candidate agent to a mixture comprising a target protein which directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises HsKif4, HsKif4b, MmKif4, XKlp1, Drosophila nod, Drosophila Klp3A, or C. elegans ChromoK-A or -B, or a fragment thereof.

Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with HsKif4 activity, and for inhibiting HsKif4.

BRIEF DESCRIPTION OF THE DRAWINGS

FIG. 1 shows an embodiment of a nucleic acid sequence encoding HsKif4 (SEQ ID NO:1).

FIG. 2 shows the amino acid sequence of HsKif4 (SEQ ID NO:2).

FIG. 3 shows an embodiment of a nucleic acid sequence encoding a particularly preferred HsKif4 construct (SEQ ID NO:3). The construct contains residues 2 through 475 of the full length HsKif4 enzyme. Sequence motifs that have been added to this HsKif4 motor domain fragment to facilitate either purification or detection of the recombinant enzyme include an N-terminal T7 epitope, a C-terminal myc epitope and 6-histidine residues at the C-terminus. The nucleotide sequence encoding these additional residues, and the corresponding amino acid sequences are indicated by boldfaced and underlined cDNA and amino acid residues.

FIG. 4 shows the amino acid sequence of a particularly preferred HsKif4 construct (SEQ ID NO:4).

FIG. 5 shows an embodiment of a nucleic acid sequence encoding a particularly preferred target protein (SEQ ID NO:5).

FIG. 6 shows the amino acid sequence of a particularly preferred target protein (SEQ ID NO:6).

FIGS. 7A and 7B show an embodiment of a nucleic acid sequence encoding HsKif4b (SEQ ID NO:7).

FIG. 8 shows the amino acid sequence of HsKif4b (SEQ ID NO:8).

DETAILED DESCRIPTION OF THE INVENTION

I. Definitions

"ADP" refers to adenosine diphosphate and also includes ADP analogs, including, but not limited to, deoxyadenosine diphosphate (dADP) and adenosine analogs.

"Biologically active" target protein refers to a target protein that has one or more of kinesin protein's biological activities, including, but not limited to microtubule stimulated ATPase activity, as tested, e.g., in an ATPase assay. Biological activity can also be demonstrated in a microtubule gliding assay or a microtubule binding assay. "ATPase activity" refers to ability to hydrolyze ATP. Other activities include polymerization/depolymerization (effects on microtubule dynamics), binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc.

Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence. Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g,. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic. Biol. Sci. 4:11–17 (1988), e.g., as implemented in the program PC/GENE (Intelligenetics, Mountain View, Calif.).

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated HsKif4 gene, the nucleic acid of interest is separated from open reading frames which flank the HsKif4 gene and encode proteins other than HsKif4. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolymerizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain of a target protein that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidine complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule stimulated ATPase activity. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to HsKif4 with the amino acid sequence encoded in SEQ ID NO:2 can be selected to obtain only those antibodies that are specifically immunoreactive with HsKif4 and not with other proteins, except for polymorphic variants, orthologs, alleles, and closely related homologues of HsKif4. This selection may be achieved by subtracting out antibodies that cross react with molecules, for example, such as C. elegans unc-104 and human Kif1A. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind" to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Bechet's disease, gout or gouty arthritis, abnormal angiogenesis accompanying: rheumatoid arthritis, psoriasis, diabetic retinopathy, and other ocular angiogenic disesase such as, macular degeneration, corneal graft rejection, corneal overgrowth, glaucoma, and Osler Webber syndrome.

II. The Target Protein

According to the present invention, a target protein is a molecule that either directly or indirectly produces ADP or phosphate and that comprises a motor domain. In a preferred embodiment, the target protein is an enzyme having activity which produces ADP and/or phosphate as a reaction product. Also included within the definition of the target proteins are amino acid sequence variants of wild-type target proteins.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein epitope tag (see, Lutz-Freyermuth et al. (1990) Proc. Natl. Acad. Sci. USA 87:6393.

In a particularly preferred embodiment, the target protein comprises HsKif4, HsKif4b, MmKif4, XKlp1, Drosophila nod, Drosophila Klp3A, or C. elegans ChromoK-A or -B, or a fragment thereof.

In another aspect of this invention, the target protein comprises an amino acid sequence which has greater than 70% sequence identity with SEQ ID NO:2, SEQ ID NO:4, SEQ ID NO:6, or SEQ ID NO:8, preferably greater than 80%, more preferably greater than 90%, more preferably greater than 95% or, in another embodiment, has 98 to 100% sequence identity with SEQ ID NO:2, SEQ ID NO:4, SEQ ID NO:6, or SEQ ID NO:8.

In a particularly preferred embodiment, a fragment of the HsKif4 protein comprising a portion of its hydrolytically active "motor" domain is used. This motor domain has been cloned and expressed in bacteria such that large quantities of biochemically active, substantially pure protein are available. Preferably, the target protein comprises an amino acid sequence which has greater than 70% sequence identity with SEQ ID NO: 4 or SEQ ID NO:6, preferably greater than 80%, more preferably greater than 90%, more preferably greater than 95% or, in another embodiment, has 98 to 100% sequence identity with SEQ ID NO: 4 or SEQ ID NO:6.

A particularly preferred embodiment is drawn to a fragment of the HsKif4 protein (SEQ ID NO:2) comprising amino acid residues 2 through 335. More preferably, this fragment is tagged at the C-terminus with a myc epitope and 6 histidines. A further preferred embodiment is drawn to a fragment of the HsKif4 protein (SEQ ID NO:2) comprising amino acid residues 2 through 679. More preferably, this fragment is tagged at the N-terminus with a T7 epitope and at the C-terminus with a myc epitope and 6 histidines.

In one aspect, the nucleic acids provided herein are defined by the proteins encoded thereby. A preferred embodiment of the invention is drawn to an isolated nucleic acid sequence encoding a microtubule motor protein, wherein the motor protein has the following properties: (i) the protein's activity includes microtubule stimulated ATPase activity; and (ii) the protein has a sequence that has greater than 70% sequence identity with SEQ ID NO:2, SEQ ID NO:4, SEQ ID NO:6, or SEQ ID NO:8, preferably greater than 80%, more preferably greater than 90%, more preferably greater than 95% or, in another embodiment, has 98 to 100% sequence identity with SEQ ID NO:2, SEQ ID NO:4 or SEQ ID NO:6. In one embodiment, the nucleic acid encodes HsKif4 or a fragment thereof. In another embodiment, the nucleic acid encodes SEQ ID NO:2, SEQ ID NO:4, SEQ ID NO:6, or SEQ ID NO:8.

In one embodiment, the nucleic acid comprises a sequence which has one or more of the following characteristics: greater than 55 or 60% sequence identity with SEQ ID NO:1, SEQ ID NO:3, SEQ ID NO:5, or SEQ ID NO:7, preferably greater than 70%, more preferably greater than 80%, more preferably greater than 90 or 95% or, in another embodiment, has 98 to 100% sequence identity with SEQ ID NO:1, SEQ ID NO:3, SEQ ID NO:5, or SEQ ID NO:7. In another embodiment provided herein, the nucleic acid hybridizes under stringent conditions to a nucleic acid having a sequence or complementary sequence of SEQ ID NO:1, SEQ ID NO:3, SEQ ID NO:5, or SEQ ID NO:7. In another embodiment, the nucleic acid has a nucleotide sequence of SEQ ID NO:1, SEQ ID NO:3, SEQ ID NO:5, or SEQ ID NO:7. As described above, when describing the nucleotide in terms of SEQ ID NO:1, SEQ ID NO:3, SEQ ID NO:5, or SEQ ID NO:7, the sequence identity may be slightly lower due to the degeneracy in the genetic code.

As will be appreciated by those in the art, the target proteins can be made in a variety of ways, including both synthesis de novo and by expressing a nucleic acid encoding the protein.

Numerous suitable methods for recombinant protein expression, including generation of expression vectors, generation of fusion proteins, introducing expression vectors into host cells, protein expression in host cells, and purifications methods are known to those in the art.

In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, and chromatofocussing. For example, the target protein can be purified using a standard anti-target antibody column. Ultrafiltration and diafiltration techniques, in conjunction with protein concentration, are also useful.

Either naturally occurring or recombinant target protein can be purified for use in functional assays. The target protein may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al. supra; and Sambrook et al., supra). A preferred method of purification is use of Ni-NTA agarose (Qiagen).

Suitable purification schemes for some specific kinesins are outlined in U.S. Ser. No. 09/295,612, filed Apr. 20, 1999, hereby expressly incorporated herein in its entirety for all purposes.

The expressed protein can be purified by standard chromatographic procedures to yield a purified, biochemically active protein. The activity of any of the peptides provided herein can be routinely confirmed by the assays provided herein such as those which assay ATPase activity or microtubule binding activity. Biologically active target protein is useful for identifying modulators of target protein or fragments thereof and kinesin superfamily members using in vitro assays such as microtubule gliding assays, ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

III. Assays for Modulators of the Target Protein

A. Functional Assays

Assays that can be used to test for modulators of the target protein include a variety of in vitro or in vivo assays, e.g., microtubule gliding assays, binding assays such as microtubule binding assays, microtubule depolymerization assays, and ATPase assays (Kodama et al., J. Biochem. 99: 1465–1472 (1986); Stewart et al., Proc. Nat'l Acad. Sci. USA 90: 5209–5213 (1993); (Lombillo et al., J. Cell Biol. 128:107–115 (1995); (Vale et al., Cell 42:39–50 (1985)).

Modulation is tested by screening for candidate agents capable of modulating the activity of the target protein comprising the steps of combining a candidate agent with the target protein, as above, and determining an alteration in the biological activity of the target protein. Thus, in this embodiment, the candidate agent should both bind to the target protein (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

In a preferred embodiment, molecular motor activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the *E. coli* phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm.

A preferred assay design is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

IV. Applications

The methods of the invention are used to identify compounds usefull in the treatment of cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

In a particularly preferred embodiment, the compositions and methods provided herein are particularly deemed useful for the inhibition of HIV and the treatment of HIV infection and AIDS. More specifically, it has been determined that Kif4 associates with retroviral Gag proteins and with murine leukemia virus Gag proteins and thus, may play a role in Gag protein transport in retrovirus-infected cells. Candidate agents that modulate the activity of Kif4 may affect transport of the Gag protein and thus, be useful in the treatment of HIV and AIDS.

In addition, the compositions provided herein can be combined with other antiviral agents or potentiators. Potentiators are materials which affect the body's response to the anti-viral agent. In the case of HIV, an adjunct therapy with AZT, 3-TC, or protease inhibitors will generally be effective.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for ATPase assays, microtubule gliding assays, or microtubule binding assays.

V. Examples

This assay is based on detection of ADP production from a target protein's microtubule stimulated ATPase. ATP production is monitored by a coupled enzyme system consisting of pyruvate kinase and lactate dehydrogenase. Under the assay conditions described below, pyruvate kianse catalyzes the conversion of ADP and phosphoenol pyruvate to pyruvate and ATP. Lactate dehydrogenase then catalyzes the oxidation-reduction reaction of pyruvate and NADH to lactate and NAD+. Thus, for each molecule of ADP produced, one molecule of NADH is consumed. The amount of NADH in the assay solution is monitored by measuring light absorbance at a wavelength of 340 nm.

The final 25 μl assay solution consists of the following: 5 μg/ml target protein, 30 μg/ml microtubules, 5 μM Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2 mM $MgCl_2$, 1 mM EGTA, 1 mM MDTT, 0.1 mg/ml BSA, 0.001% antifoam 289, and 1 mM ATP.

Potential candidate agents are dissolved in DMSO at a concentration of about 1 mg/ml and 0.5 μl of each chemical solution is dispensed into a single well of a clear 384 well plate. Each of the 384 wells are then filled with 20 μl of a solution consisting of all of the assay components described above except for ATP. The plate is agitated at a high frequency. To start the assay, 5 μl of a solution containing ATP is added to each well. The plate is agitated and the absorbance is read at 340 nm over various time intervals. The assay is run at room temperature.

The assay components and the performance of the assay are optimized together to match the overall read time with the rate of the target protein's ADP production. The read time should be long enough for the rate of NADH consumption to reach steady state beyond an initial lag time of several seconds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

---

What is claimed is:

1. A method for screening for modulators of a target protein, wherein the target protein has microtubule stimulated ATPase activity and comprises SEQ ID NO:2, the method comprising the steps of contacting the target protein with a candidate agent at a first concentration and determining a level of activity of the target protein; and contacting the target protein with a candidate agent at a second concentration and determining a level of activity of the target protein;

wherein the activity is selected from the group consisting of binding activity or ATPase activity, and wherein a difference between the level of activity of the target protein contacted with the first concentration of the candidate agent and the level of activity of the target protein contacted with the second concentration of the candidate agent indicates that the candidate agent modulates the activity of the target protein.

2. A method for screening for modulators of a target protein, wherein the target protein has microtubule stimulated ATPase activity and comprises SEQ ID NO:4, the method comprising the steps of:

contacting the target protein with a candidate agent at a first concentration and determining a level of activity of the target protein; and contacting the target protein with a candidate agent at a second concentration and determining a level of activity of the target protein;

wherein the activity is selected from the group consisting of binding activity or ATPase activity, and wherein a difference between the level of activity of the target protein contacted with the first concentration of the candidate agent and the level of activity of the target protein contacted with the second concentration of the candidate agent indicates that the candidate agent modulates the activity of the target protein.

3. A method for screening for modulators of a target protein, wherein the target protein has microtubule stimulated ATPase activity and comprises SEQ ID NO:6, the method comprising the steps of:

contacting the target protein with a candidate agent at a first concentration and determining a level of activity of the target protein; and contacting the target protein with a candidate agent at a second concentration and determining a level of activity of the target protein;

wherein the activity is selected from the group consisting of binding activity or ATPase activity, and wherein a difference between the level of activity of the target protein contacted with the first concentration of the candidate agent and the level of activity of the target protein contacted with the second concentration of the candidate agent indicates that the candidate agent modulates the activity of the target protein.

4. The method of claim 1, 2, or 3, wherein said determining occurs by a fluorescent, luminescent, radioactive, or absorbance readout.

5. The method of claim 1, 2, or 3, wherein said level of activity of said reaction is determined at multiple time points.

6. The method of claim 1, 2, or 3, wherein said method further comprises the steps of:

culturing one or more cells that express the target protein;

adding said candidate agent to said cells; and determining the effect of said candidate agent on said cells.

7. The method of claim 6, wherein said culturing step is conducted in a stationary multiwell plate.

8. The method of claim 7, wherein the multiwell plate is a 96- or 384-well microtiter plate.

9. The method of claim 1, 2, or 3, wherein the target protein has been isolated from an endogenous source.

10. The method of claim 1, 2, or 3, wherein the target protein has been produced recombinantly.

11. The method of claim 1, 2, or 3, wherein said first or second concentration of the candidate agent is zero or at a level below detection.

12. The method of claim 1, 2, or 3, wherein the candidate agent is an agonist.

13. The method of claim 1, 2, or 3, wherein the candidate agent is an antagonist.

14. The method of claim 1, 2, or 3, wherein the candidate agent binds to the target protein.

15. The method of claim 1, 2, or 3, wherein the target protein is contacted with the candidate agent in vivo.

16. The method of claim 1, 2, or 3, wherein the target protein is contacted with the candidate agent in vitro.

17. The method of claim 1, 2, or 3, wherein determining the level of activity of the target protein comprises screening for alterations in cell cycle distribution or cell viability.

18. The method of claim 1, 2, or 3, wherein determining the level of activity of the target protein comprises screening for the presence, morphology, activity, distribution, or amount of mitotic spindles.

19. The method of claim 1, 2, or 3, wherein contacting the target protein with a candidate agent comprises adding the candidate agent to a mixture comprising the target protein under conditions which normally allow the production of ADP or phosphate.

20. A method of claim 19, wherein determining the level of activity of the target protein comprises the steps of:

i) subjecting the mixture to an enzymatic reaction, wherein said enzymatic reaction uses ADP or phosphate as a substrate under conditions which normally allow the ADP or phosphate to be utilized; and ii) measuring NADH consumption as a measure of ADP production, wherein a change in measure of NADH consumption between the first and second concentrations of the candidate agent indicates that the candidate agent is a modulator of the target protein.

21. The method of claim 1, 2, or 3, wherein the candidate agent is labeled.

* * * * *

SEQUENCE LISTING

<160> NUMBER OF SEQ ID NOS: 8

<210> SEQ ID NO 1
<211> LENGTH: 4308
<212> TYPE: DNA
<213> ORGANISM: Human

<400> SEQUENCE: 1

-continued

| | | | | |
|---|---|---|---|---|
| gggaggccca | gggagaacgg | ggaagggaca | tttagtttga | gacggtgctg | agataggatc | 60 |
| atgaaggaag | aggtgaaggg | aattcctgta | agagtggcgc | tgcgttgtcg | ccctctggtc | 120 |
| cccaaagaga | ttagcgaggg | ctgccagatg | tgcctttcct | tcgtgcccgg | agagcctcag | 180 |
| gtggtggttg | gtacagataa | atccttcacc | tacgattttg | tatttgatcc | ctctactgaa | 240 |
| caggaagaag | tcttcaatac | agcagtagcg | ccactcataa | aaggtgtatt | taaaggatat | 300 |
| aatgcaacgg | tcctggccta | tgggcagact | ggctctggaa | aaacctattc | aatgggaggt | 360 |
| gcatatactg | cagagcaaga | gaatgaacca | acagttgggg | ttattcctag | ggtaatacaa | 420 |
| ctgctcttca | aagaaattga | taaaaagagt | gactttgaat | ttactctgaa | agtgtcttac | 480 |
| ttagagattt | acaatgaaga | aattttggat | cttctatgtc | catctcgtga | gaaagctcaa | 540 |
| ttagagattt | acaatgaaga | aattttggat | cttctatgtc | catctcgtga | gaaagctcaa | 600 |
| gttttggttg | ccttggatac | tgtttcctgt | ttggaacagg | gcaacaactc | taggactgtg | 660 |
| gcctccacgg | ctatgaactc | ccagtcgtcc | cgatctcatg | ccatcttaac | aatctcctta | 720 |
| gagcaaggaa | agaaaagtga | caagaatagc | agctttcgct | ccaagctgca | tcttgtagac | 780 |
| ctcgctggat | cagaaagaca | gaagaaaacc | aaggctgaag | gggatcgtct | aaaagagggt | 840 |
| attaatatta | accgaggcct | cctatgcttg | ggaaatgtaa | tcagtgctct | tggagatgac | 900 |
| aaaaagggtg | gctttgcgcc | ctacagagat | tccaagttga | ctcgactgct | tcaagattct | 960 |
| ctaggaggta | atagccatac | tcttatgata | gcctgtgtga | gtcctgctga | ctccaatcta | 1020 |
| gaggaaacat | taaatacct | tcgctatgct | gacagagcaa | gaaaaatcaa | gaacaaacct | 1080 |
| attgttaata | ttgatcccca | gacagctgaa | cttaatcatc | taaagcaaca | ggtacaacag | 1140 |
| ctacaagtct | tgttgctaca | ggcccatgga | ggtaccctgc | ctggatctat | aactgtggaa | 1200 |
| ccatcagaga | atctacaatc | cctgatggag | aagaatcagt | ccctggtaga | ggagaatgaa | 1260 |
| aaattaagtc | gtggtctgag | cgaggcagct | ggtcagacag | cccagatgtt | ggagaggatc | 1320 |
| atttggacag | agcaagcgaa | tgaaaaaatg | aacgccaagc | tagaagagct | caggcagcat | 1380 |
| gcggcctgca | aactggatct | tcaaaagcta | gtggagactt | tggaagacca | ggaattgaaa | 1440 |
| gaaaatgtag | agataatttg | taacctgcag | caattgatta | cccagttatc | ggatgaaact | 1500 |
| gttgcttgca | tggctgcagc | cattgatact | gcggtggagc | aagaagccca | agtagaaacc | 1560 |
| agtccagaga | cgagcaggtc | ttctgacgct | tttaccactc | agcatgctct | ccgtcaagcg | 1620 |
| cagatgtcta | aggagctggt | tgagttgaat | aaagcgcttg | cactgaaaga | ggccctggct | 1680 |
| aggaagatga | ctcagaatga | cagccaactg | cagcctattc | agtaccaata | ccaggataac | 1740 |
| ataaagagc | cagaattaga | agtcatcaat | ctgcaaaagg | aaaaggaaga | attggttctt | 1800 |
| gaacttcaga | cagcaaagaa | ggatgccaac | caagccaagt | tgagtgagcg | ccgccgcaaa | 1860 |
| cgtctccagg | agctggaggg | tcaaattgct | gatctgaaga | agaaactgaa | tgagcagtcc | 1920 |
| aaacttctga | actaaaagga | atccacagag | cgtactgtct | ccaaactgaa | ccaggagata | 1980 |
| cggatgatga | aaaccagcg | ggtacagtta | atgcgtcaaa | tgaaagaaga | tgctgagaag | 2040 |
| tttagacagt | ggaagcagaa | aagagacaaa | gaagtaatac | agttaaaaga | acgagaccgt | 2100 |
| aagaggcaat | atgagctgct | gaaacttgaa | agaaacttcc | agaaacaatc | caatgtgctc | 2160 |
| agacgtaaaa | cggaggaggc | agcagctgcc | aacaagcgtc | tcaaggatgc | tctccagaaa | 2220 |
| caacgggagg | ttgcagataa | gcggaaagag | actcagagcc | gtggaatgga | aggcactgca | 2280 |
| gctcgagtga | agaattggct | tggaaacgaa | attgaggtta | tggtcagtac | tgaggaagcc | 2340 |
| aaacgccatc | tgaatgacct | ccttgaagat | agaaagatcc | tggctcaaga | tgtggctcaa | 2400 |

-continued

| | |
|---|---|
| ctcaaagaaa aaaaggaatc tggggagaat ccacctccta aactccggag gcgtacattc | 2460 |
| tcccttactg aagtgcgtgg tcaagtttcg gagtcagaag attctattac aaagcagatt | 2520 |
| gaaagcctag agactgaaat ggaattcagg agtgctcaga ttgctgacct acagcagaag | 2580 |
| ctgctggatg cagaaagtga agacagacca aacaacgct gggagaatat tgccaccatt | 2640 |
| ctggaagcca agtgtgccct gaaatatttg attggagagc tggtctcctc caaaatacag | 2700 |
| gtcagcaaac ttgaaagcag cctgaaacag agcaagacca gctgtgctga catgcagaag | 2760 |
| atgctgtttg aggaacgaaa tcattttgcc gagatagaga cagagttaca agctgagctg | 2820 |
| gtcagaatgg agcaacagca cccagagaag gtgctgtacc ttctcagcca gctgcagcaa | 2880 |
| agccaaatgg cagagaagca gttagaggaa tcagtcagtg aaaaggaaca gcagctgcaa | 2940 |
| agcacactga agtgtcagga tgaagaactt gagaaaatgc gagaagtgtg tgagcaaaat | 3000 |
| cagcagcttc tccgagagaa tgaaatcatc aagcagaaac tgaccctcct ccaggtagcc | 3060 |
| agcagacaga aacatcttcc taaggatacc cttctatctc cagactcttc ttttgaatat | 3120 |
| gtccagccta agccaaaacc ttctcgtgtt aaagaaaagt tcctggagca aagcatggac | 3180 |
| atcgaggatc taaaatattg ttcagagcat tctgtgaatg agcatgagga tggtgatggt | 3240 |
| gatgatgatg aggggatga cgaggaatgg aagccaacaa aattagttaa tgtgtccagg | 3300 |
| aagaacatcc aagggtgttc ctgcaagggc tggtgtggaa acaagcaatg tgggtgcagg | 3360 |
| aagcaaaagt cagactgtgg tgtggactgt tgctgtgacc ccacaaagtg tcggaaccgc | 3420 |
| cagcaaggca aggatagctt gggcactgtt gaacggaccc aggattcaga aagctccttc | 3480 |
| aaactggagg atcctaccga ggtgacccca ggattgagct tctttaatcc cgtctgtgcc | 3540 |
| accccccaata gcaagatcct gaaagagatg tgcgatgtgg agcaggtgct gtcaaagaag | 3600 |
| actcccccag ctccctcccc ttttgacctc ccagagttaa aacatgtagc aacagaatac | 3660 |
| caagaaaaca agggctccgg gaagaaaaag aaacgggctc tggccagcaa caccagcttc | 3720 |
| ttctctggct gctcccctat cgaagaagag gcccactgaa gttggagtca tcatctctac | 3780 |
| ccccagtctg gcttgggaga tgcttt cagg ttgcagccag aaggggttt taatgactct | 3840 |
| ctgattcagt tcttgctgtt gaaaaggaac aagcgttact gaaaagaagg taacctttgt | 3900 |
| tggatgtggg ccttagcctc caggtccaga ctactactgt atgttctcca gaagggtgct | 3960 |
| aagtcaccta cgaagagaga accaacagac tttcctattg actcatcagg aaccagtcct | 4020 |
| cagtctggtc aagttgtttc ttatttgtga gcagttcagg ccatctcctg atggggatga | 4080 |
| ggccaaggct ttcttatctt ttggtcgtct ccgcttaatg gaggagcctg gcctaggatg | 4140 |
| gaggcctggc ttagatcttt cattccacct caagaatgag gttgtgatct ttcctgtcct | 4200 |
| gaccctctct gaattatgtt tcaatagtac tcttgattgt ctgccatgtt gttgaagcaa | 4260 |
| atgaattatt tttaaatgtt aagtaagtaa ataaaccttta gcccgtct | 4308 |

<210> SEQ ID NO 2
<211> LENGTH: 1232
<212> TYPE: PRT
<213> ORGANISM: Human

<400> SEQUENCE: 2

Met Lys Glu Glu Val Lys Gly Ile Pro Val Arg Val Ala Leu Arg Cys
1               5                   10                  15

Arg Pro Leu Val Pro Lys Glu Ile Ser Glu Gly Cys Gln Met Cys Leu
            20                  25                  30

-continued

```
Ser Phe Val Pro Gly Glu Pro Gln Val Val Gly Thr Asp Lys Ser
        35                  40                  45

Phe Thr Tyr Asp Phe Val Phe Asp Pro Ser Thr Glu Gln Glu Val
        50                  55                  60

Phe Asn Thr Ala Val Ala Pro Leu Ile Lys Gly Val Phe Lys Gly Tyr
65                      70                  75                  80

Asn Ala Thr Val Leu Ala Tyr Gly Gln Thr Gly Ser Gly Lys Thr Tyr
                    85                  90                  95

Ser Met Gly Gly Ala Tyr Thr Ala Glu Gln Glu Asn Glu Pro Thr Val
                100                 105                 110

Gly Val Ile Pro Arg Val Ile Gln Leu Leu Phe Lys Glu Ile Asp Lys
                115                 120                 125

Lys Ser Asp Phe Glu Phe Thr Leu Lys Val Ser Tyr Leu Glu Ile Tyr
        130                 135                 140

Asn Glu Glu Ile Leu Asp Leu Leu Cys Pro Ser Arg Glu Lys Ala Gln
145                 150                 155                 160

Ile Asn Ile Arg Glu Asp Pro Lys Glu Gly Ile Lys Ile Val Gly Leu
                165                 170                 175

Thr Glu Lys Thr Val Leu Val Ala Leu Asp Thr Val Ser Cys Leu Glu
                180                 185                 190

Gln Gly Asn Asn Ser Arg Thr Val Ala Ser Thr Ala Met Asn Ser Gln
                195                 200                 205

Ser Ser Arg Ser His Ala Ile Leu Thr Ile Ser Leu Glu Gln Gly Lys
        210                 215                 220

Lys Ser Asp Lys Asn Ser Ser Phe Arg Ser Lys Leu His Leu Val Asp
225                 230                 235                 240

Leu Ala Gly Ser Glu Arg Gln Lys Lys Thr Lys Ala Glu Gly Asp Arg
                245                 250                 255

Leu Lys Glu Gly Ile Asn Ile Asn Arg Gly Leu Leu Cys Leu Gly Asn
                260                 265                 270

Val Ile Ser Ala Leu Gly Asp Asp Lys Lys Gly Gly Phe Ala Pro Tyr
                275                 280                 285

Arg Asp Ser Lys Leu Thr Arg Leu Leu Gln Asp Ser Leu Gly Gly Asn
290                 295                 300

Ser His Thr Leu Met Ile Ala Cys Val Ser Pro Ala Asp Ser Asn Leu
305                 310                 315                 320

Glu Glu Thr Leu Asn Thr Leu Arg Tyr Ala Asp Arg Ala Arg Lys Ile
                325                 330                 335

Lys Asn Lys Pro Ile Val Asn Ile Asp Pro Gln Thr Ala Glu Leu Asn
                340                 345                 350

His Leu Lys Gln Gln Val Gln Gln Leu Gln Val Leu Leu Leu Gln Ala
        355                 360                 365

His Gly Gly Thr Leu Pro Gly Ser Ile Thr Val Glu Pro Ser Glu Asn
        370                 375                 380

Leu Gln Ser Leu Met Glu Lys Asn Gln Ser Leu Val Glu Glu Asn Glu
385                 390                 395                 400

Lys Leu Ser Arg Gly Leu Ser Glu Ala Ala Gly Gln Thr Ala Gln Met
                405                 410                 415

Leu Glu Arg Ile Ile Trp Thr Gln Ala Asn Glu Lys Met Asn Ala
                420                 425                 430

Lys Leu Glu Glu Leu Arg Gln His Ala Ala Cys Lys Leu Asp Leu Gln
        435                 440                 445

Lys Leu Val Glu Thr Leu Glu Asp Gln Glu Leu Lys Glu Asn Val Glu
```

```
                450                 455                 460
Ile Ile Cys Asn Leu Gln Gln Leu Ile Thr Gln Leu Ser Asp Glu Thr
465                 470                 475                 480

Val Ala Cys Met Ala Ala Ile Asp Thr Ala Val Glu Gln Glu Ala
                485                 490                 495

Gln Val Glu Thr Ser Pro Glu Thr Ser Arg Ser Ser Asp Ala Phe Thr
                500                 505                 510

Thr Gln His Ala Leu Arg Gln Ala Gln Met Ser Lys Glu Leu Val Glu
            515                 520                 525

Leu Asn Lys Ala Leu Ala Leu Lys Glu Ala Leu Ala Arg Lys Met Thr
            530                 535                 540

Gln Asn Asp Ser Gln Leu Gln Pro Ile Gln Tyr Gln Tyr Gln Asp Asn
545                 550                 555                 560

Ile Lys Glu Pro Glu Leu Glu Val Ile Asn Leu Gln Lys Glu Lys Glu
                565                 570                 575

Glu Leu Val Leu Glu Leu Gln Thr Ala Lys Lys Asp Ala Asn Gln Ala
            580                 585                 590

Lys Leu Ser Glu Arg Arg Lys Arg Leu Gln Glu Leu Glu Gly Gln
            595                 600                 605

Ile Ala Asp Leu Lys Lys Lys Leu Asn Glu Gln Ser Lys Leu Leu Lys
610                 615                 620

Leu Lys Glu Ser Thr Glu Arg Thr Val Ser Lys Leu Asn Gln Glu Ile
625                 630                 635                 640

Arg Met Met Lys Asn Gln Arg Val Gln Leu Met Arg Gln Met Lys Glu
                645                 650                 655

Asp Ala Glu Lys Phe Arg Gln Trp Lys Gln Lys Arg Asp Lys Glu Val
                660                 665                 670

Ile Gln Leu Lys Glu Arg Asp Arg Lys Arg Gln Tyr Glu Leu Leu Lys
            675                 680                 685

Leu Glu Arg Asn Phe Gln Lys Gln Ser Asn Val Leu Arg Arg Lys Thr
690                 695                 700

Glu Glu Ala Ala Ala Ala Asn Lys Arg Leu Lys Asp Ala Leu Gln Lys
705                 710                 715                 720

Gln Arg Glu Val Ala Asp Lys Arg Lys Glu Thr Gln Ser Arg Gly Met
                725                 730                 735

Glu Gly Thr Ala Ala Arg Val Lys Asn Trp Leu Gly Asn Glu Ile Glu
            740                 745                 750

Val Met Val Ser Thr Glu Glu Ala Lys Arg His Leu Asn Asp Leu Leu
            755                 760                 765

Glu Asp Arg Lys Ile Leu Ala Gln Asp Val Ala Gln Leu Lys Glu Lys
            770                 775                 780

Lys Glu Ser Gly Glu Asn Pro Pro Lys Leu Arg Arg Arg Thr Phe
785                 790                 795                 800

Ser Leu Thr Glu Val Arg Gly Gln Val Ser Glu Ser Glu Asp Ser Ile
                805                 810                 815

Thr Lys Gln Ile Glu Ser Leu Glu Thr Glu Met Glu Phe Arg Ser Ala
            820                 825                 830

Gln Ile Ala Asp Leu Gln Gln Lys Leu Leu Asp Ala Glu Ser Glu Asp
            835                 840                 845

Arg Pro Lys Gln Arg Trp Glu Asn Ile Ala Thr Ile Leu Glu Ala Lys
            850                 855                 860

Cys Ala Leu Lys Tyr Leu Ile Gly Glu Leu Val Ser Ser Lys Ile Gln
865                 870                 875                 880
```

-continued

Val Ser Lys Leu Glu Ser Ser Leu Lys Gln Ser Lys Thr Ser Cys Ala
            885                 890                 895

Asp Met Gln Lys Met Leu Phe Glu Arg Asn His Phe Ala Glu Ile
        900                 905                 910

Glu Thr Glu Leu Gln Ala Glu Leu Val Arg Met Glu Gln Gln His Pro
            915                 920                 925

Glu Lys Val Leu Tyr Leu Leu Ser Gln Leu Gln Gln Ser Gln Met Ala
        930                 935                 940

Glu Lys Gln Leu Glu Glu Ser Val Ser Glu Lys Glu Gln Leu Gln
945                 950                 955                 960

Ser Thr Leu Lys Cys Gln Asp Glu Glu Leu Glu Lys Met Arg Glu Val
            965                 970                 975

Cys Glu Gln Asn Gln Gln Leu Leu Arg Glu Asn Glu Ile Ile Lys Gln
        980                 985                 990

Lys Leu Thr Leu Leu Gln Val Ala Ser Arg Gln Lys His Leu Pro Lys
        995                 1000                1005

Asp Thr Leu Leu Ser Pro Asp Ser Ser Phe Glu Tyr Val Gln Pro Lys
        1010                1015                1020

Pro Lys Pro Ser Arg Val Lys Glu Lys Phe Leu Glu Gln Ser Met Asp
1025                1030                1035                1040

Ile Glu Asp Leu Lys Tyr Cys Ser Glu His Ser Val Asn Glu His Glu
            1045                1050                1055

Asp Gly Asp Gly Asp Asp Glu Gly Asp Glu Glu Trp Lys Pro
        1060                1065                1070

Thr Lys Leu Val Asn Val Ser Arg Lys Asn Ile Gln Gly Cys Ser Cys
            1075                1080                1085

Lys Gly Trp Cys Gly Asn Lys Gln Cys Gly Cys Arg Lys Gln Lys Ser
        1090                1095                1100

Asp Cys Gly Val Asp Cys Cys Cys Asp Pro Thr Lys Cys Arg Asn Arg
1105                1110                1115                1120

Gln Gln Gly Lys Asp Ser Leu Gly Thr Val Glu Arg Thr Gln Asp Ser
            1125                1130                1135

Glu Ser Ser Phe Lys Leu Glu Asp Pro Thr Glu Val Thr Pro Gly Leu
        1140                1145                1150

Ser Phe Phe Asn Pro Val Cys Ala Thr Pro Asn Ser Lys Ile Leu Lys
        1155                1160                1165

Glu Met Cys Asp Val Glu Gln Val Leu Ser Lys Thr Pro Pro Ala
        1170                1175                1180

Pro Ser Pro Phe Asp Leu Pro Glu Leu Lys His Val Ala Thr Glu Tyr
1185                1190                1195                1200

Gln Glu Asn Lys Gly Ser Gly Lys Lys Lys Arg Ala Leu Ala Ser
            1205                1210                1215

Asn Thr Ser Phe Phe Ser Gly Cys Ser Pro Ile Glu Glu Ala His
            1220                1225                1230

<210> SEQ ID NO 3
<211> LENGTH: 1569
<212> TYPE: DNA
<213> ORGANISM: Human

<400> SEQUENCE: 3
atggctagca tgactggtgg acagcaaatg ggtcggatcc gaattcgagc tccgtcgaca    60
agcttggaag aggtgaaggg aattcctgta agagtggcgc tgcgttgtcg ccctctggtc   120

-continued

```
cccaaagaga ttagcgaggg ctgccagatg tgcctttcct tcgtgcccgg agagcctcag      180
gtggtggttg gtacagataa atccttcacc tacgattttg tatttgatcc ctctactgaa      240
caggaagaag tcttcaatac agcagtagcg ccactcataa aggtgtgtatt taaaggatat     300 aatgcaacgg tcctggccta tgggcagact ggctctggaa aaacctattc aatgggaggt     360
gcatatactg cagagcaaga gaatgaacca acagttgggg ttattcctag ggtaatacaa      420
ctgctcttca aagaaattga taaaagagt gactttgaat ttactctgaa agtgtcttac       480
ttagagattt acaatgaaga aattttggat cttctatgcc catctcgtga aaagctcaa       540 ataaatatac gagaggatcc taaggaaggc ataaagattg tgggactcac tgagaagact      600
gttttggttg ccttggatac tgtttcctgt ttggaacagg gcaacaactc taggactgtg      660
gcctccacgg ctatgaactc ccagtcgtcc cgatctcatg ccatctttac aatctcctta     720
gagcaaagaa agaaaagtga caagaatagc agctttcgct ccaagctgca tcttgtagac      780
ctcgctggat cagaaagaca gaagaaaacc aaggctgaag gggatcgtct aaaagagggt      840
attaatatta accgaggcct ccctatgcttg ggaaatgtaa tcagtgctct tggagatgac    900
aaaaagggtg gctttgtgcc ctacagagat tccaagttga ctcgactgct tcaagattct     960
ctaggaggta atagccatac tcttatgata gcctgtgtga gtcctgctga ctccaatcta    1020
gaggaaacat taaatacccct tcgctatgct gacagagcaa gaaaaatcaa gaacaaacct   1080
attgttaata ttgatcccca gacagctgaa cttaatcatc taaagcaaca ggtacaacag    1140
ctacaagtct tgttgctaca ggcccatgga ggtaccctgc ctggatctat aactgtggaa    1200
ccatcagaga atctcaaatc cctgatggag aagaatcagt ccctggtaga ggagaatgaa    1260
aaattaagtc gtggtctgag cgaggcagct ggtcagacag cccagatgtt ggagaggatc    1320
atttggacag agcaagcgaa tgaaaaaatg aacgccaagc tagaagagct caggcagcat    1380
gcggcctgca aactggatct tcaaaagcta gtggagactt tggaagacca ggaattgaaa    1440
gaaaatgtag agataatttg taacctgcag caattgatta cccagaagct gcggccgca    1500 ctcgagggta ccgagcagaa gctgatcagc gaggaggacc tgatcgagca ccaccaccac    1560
caccactga                                                            1569
```

<210> SEQ ID NO 4
<211> LENGTH: 522
<212> TYPE: PRT
<213> ORGANISM: Human

<400> SEQUENCE: 4

```
Met Ala Ser Met Thr Gly Gly Gln Gln Met Gly Arg Ile Arg Ile
 1               5                  10                  15

Ala Pro Ser Thr Ser Leu Glu Glu Val Lys Gly Ile Pro Val Arg Val
                20                  25                  30

Ala Leu Arg Cys Arg Pro Leu Val Pro Lys Glu Ile Ser Glu Gly Cys
            35                  40                  45

Gln Met Cys Leu Ser Phe Val Pro Gly Glu Pro Gln Val Val Gly
        50                  55                  60

Thr Asp Lys Ser Phe Thr Tyr Asp Phe Val Asp Pro Ser Thr Glu
65                  70                  75                  80

Gln Glu Glu Val Phe Asn Thr Ala Val Ala Pro Leu Ile Lys Gly Val
                85                  90                  95

Phe Lys Gly Tyr Asn Ala Thr Val Leu Ala Tyr Gly Gln Thr Gly Ser
            100                 105                 110
```

```
Gly Lys Thr Tyr Ser Met Gly Gly Ala Tyr Thr Ala Glu Gln Glu Asn
        115                 120                 125

Glu Pro Thr Val Gly Val Ile Pro Arg Val Ile Gln Leu Leu Phe Lys
130                 135                 140

Glu Ile Asp Lys Lys Ser Asp Phe Glu Phe Thr Leu Lys Val Ser Tyr
145                 150                 155                 160

Leu Glu Ile Tyr Asn Glu Glu Ile Leu Asp Leu Leu Cys Pro Ser Arg
                165                 170                 175

Glu Lys Ala Gln Ile Asn Ile Arg Glu Asp Pro Lys Glu Gly Ile Lys
            180                 185                 190

Ile Val Gly Leu Thr Glu Lys Thr Val Leu Val Ala Leu Asp Thr Val
        195                 200                 205

Ser Cys Leu Glu Gln Gly Asn Ser Arg Thr Val Ala Ser Thr Ala
210                 215                 220

Met Asn Ser Gln Ser Ser Arg Ser His Ala Ile Phe Thr Ile Ser Leu
225                 230                 235                 240

Glu Gln Arg Lys Lys Ser Asp Lys Asn Ser Ser Phe Arg Ser Lys Leu
                245                 250                 255

His Leu Val Asp Leu Ala Gly Ser Glu Arg Gln Lys Lys Thr Lys Ala
            260                 265                 270

Glu Gly Asp Arg Leu Lys Glu Gly Ile Asn Ile Asn Arg Gly Leu Leu
        275                 280                 285

Cys Leu Gly Asn Val Ile Ser Ala Leu Gly Asp Asp Lys Lys Gly Gly
    290                 295                 300

Phe Val Pro Tyr Arg Asp Ser Lys Leu Thr Arg Leu Leu Gln Asp Ser
305                 310                 315                 320

Leu Gly Gly Asn Ser His Thr Leu Met Ile Ala Cys Val Ser Pro Ala
                325                 330                 335

Asp Ser Asn Leu Glu Glu Thr Leu Asn Thr Leu Arg Tyr Ala Asp Arg
            340                 345                 350

Ala Arg Lys Ile Lys Asn Lys Pro Ile Val Asn Ile Asp Pro Gln Thr
        355                 360                 365

Ala Glu Leu Asn His Leu Lys Gln Gln Val Gln Gln Leu Gln Val Leu
370                 375                 380

Leu Leu Gln Ala His Gly Gly Thr Leu Pro Gly Ser Ile Thr Val Glu
385                 390                 395                 400

Pro Ser Glu Asn Leu Gln Ser Leu Met Glu Lys Asn Gln Ser Leu Val
                405                 410                 415

Glu Glu Asn Glu Lys Leu Ser Arg Gly Leu Ser Glu Ala Ala Gly Gln
            420                 425                 430

Thr Ala Gln Met Leu Glu Arg Ile Ile Trp Thr Glu Gln Ala Asn Glu
        435                 440                 445

Lys Met Asn Ala Lys Leu Glu Glu Leu Arg Gln His Ala Ala Cys Lys
    450                 455                 460

Leu Asp Leu Gln Lys Leu Val Glu Thr Leu Glu Asp Gln Glu Leu Lys
465                 470                 475                 480

Glu Asn Val Glu Ile Ile Cys Asn Leu Gln Gln Leu Ile Thr Gln Lys
                485                 490                 495

Leu Ala Ala Ala Leu Glu Gly Thr Glu Gln Lys Leu Ile Ser Glu Glu
            500                 505                 510

Asp Leu Ile Glu His His His His His His
        515                 520
```

-continued

```
<210> SEQ ID NO 5
<211> LENGTH: 1421
<212> TYPE: DNA
<213> ORGANISM: Human

<400> SEQUENCE: 5
tggaagaggt gaagggaatt cctgtaagag tggcgctgcg ttgtcgccct ctggtcccca       60
aagagattag cgagggctgc cagatgtgcc tttccttcgt gcccggagag cctcaggtgg      120
tggttggtac agataaatcc ttcacctacg attttgtatt tgatccctct actgaacagg      180
aagaagtctt caatacagca gtagcgccac tcataaaagg tgtatttaaa ggatataatg      240
caacggtcct ggcctatggg cagactggct ctggaaaaac ctattcaatg ggaggtgcat      300
atactgcaga gcaagagaat gaaccaacag ttggggttat cctagggta atacaactgc       360
tcttcaaaga aattgataaa aagagtgact tgaatttac tctgaaagtg tcttacttag       420
agatttacaa tgaagaaatt tggatcttc tatgcccatc tcgtgagaaa gctcaaataa       480
atatacgaga ggatcctaag gaaggcataa agattgtggg actcactgag aagactgttt      540
tggttgcctt ggatactgtt tcctgtttgg aacagggcaa caactctagg actgtggcct      600
ccacggctat gaactcccag tcgtcccgat ctcatgccat ctttacaatc tccttagagc      660
aaagaaagaa aagtgacaag aatagcagct tcgctccaa gctgcatctt gtagacctcg       720
ctggatcaga agacagaag aaaaccaagg ctgaagggga tcgtctaaaa gagggtatta      780
atattaaccg aggcctccta tgcttgggaa atgtaatcag tgctcttgga gatgacaaaa      840
agggtggctt tgtgccctac agagattcca agttgactcg actgcttcaa gattctctag      900
gaggtaatag ccatactctt atgatagcct gtgtgagtcc tgctgactcc aatctagagg      960
aaacattaaa taccttcgc tatgctgaca gagcaagaaa aatcaagaac aaacctattg      1020
ttaatattga tccccagaca gctgaactta atcatctaaa gcaacaggta caacagctac     1080
aagtcttgtt gctacaggcc catggaggta ccctgcctgg atctataact gtggaaccat     1140
cagagaatct acaatccctg atggagaaga atcagtccct ggtagaggag aatgaaaaat     1200
taagtcgtgg tctgagcgag gcagctggtc agacagccca gatgttggag aggatcattt     1260
ggacagagca agcgaatgaa aaaatgaacg ccaagctaga agagctcagg cagcatgcgg     1320
cctgcaaact ggatcttcaa aagctagtgg agactttgga agaccaggaa ttgaaagaaa     1380
atgtagagat aatttgtaac ctgcagcaat tgattaccca g                          1421

<210> SEQ ID NO 6
<211> LENGTH: 473
<212> TYPE: PRT
<213> ORGANISM: Human

<400> SEQUENCE: 6

Glu Glu Val Lys Gly Ile Pro Val Arg Val Ala Leu Arg Cys Arg Pro
 1               5                  10                  15

Leu Val Pro Lys Glu Ile Ser Glu Gly Cys Gln Met Cys Leu Ser Phe
            20                  25                  30

Val Pro Gly Glu Pro Gln Val Val Gly Thr Asp Lys Ser Phe Thr
        35                  40                  45

Tyr Asp Phe Val Phe Asp Pro Ser Thr Glu Gln Glu Val Phe Asn
    50                  55                  60

Thr Ala Val Ala Pro Leu Ile Lys Gly Val Phe Lys Gly Tyr Asn Ala
65                  70                  75                  80

Thr Val Leu Ala Tyr Gly Gln Thr Gly Ser Gly Lys Thr Tyr Ser Met
```

-continued

```
                    85                  90                  95
Gly Gly Ala Tyr Thr Ala Glu Gln Glu Asn Glu Pro Thr Val Gly Val
                100                 105                 110

Ile Pro Arg Val Ile Gln Leu Leu Phe Lys Glu Ile Asp Lys Lys Ser
            115                 120                 125

Asp Phe Glu Phe Thr Leu Lys Val Ser Tyr Leu Glu Ile Tyr Asn Glu
130                 135                 140

Glu Ile Leu Asp Leu Leu Cys Pro Ser Arg Glu Lys Ala Gln Ile Asn
145                 150                 155                 160

Ile Arg Glu Asp Pro Lys Glu Gly Ile Lys Ile Val Gly Leu Thr Glu
                165                 170                 175

Lys Thr Val Leu Val Ala Leu Asp Thr Val Ser Cys Leu Glu Gln Gly
            180                 185                 190

Asn Asn Ser Arg Thr Val Ala Ser Thr Ala Met Asn Ser Gln Ser Ser
        195                 200                 205

Arg Ser His Ala Ile Phe Thr Ile Ser Leu Glu Gln Arg Lys Lys Ser
    210                 215                 220

Asp Lys Asn Ser Ser Phe Arg Ser Lys Leu His Leu Val Asp Leu Ala
225                 230                 235                 240

Gly Ser Glu Arg Gln Lys Lys Thr Lys Ala Glu Gly Asp Arg Leu Lys
                245                 250                 255

Glu Gly Ile Asn Ile Asn Arg Gly Leu Leu Cys Leu Gly Asn Val Ile
            260                 265                 270

Ser Ala Leu Gly Asp Asp Lys Lys Gly Gly Phe Val Pro Tyr Arg Asp
        275                 280                 285

Ser Lys Leu Thr Arg Leu Leu Gln Asp Ser Leu Gly Gly Asn Ser His
    290                 295                 300

Thr Leu Met Ile Ala Cys Val Ser Pro Ala Asp Ser Asn Leu Glu Glu
305                 310                 315                 320

Thr Leu Asn Thr Leu Arg Tyr Ala Asp Arg Ala Arg Lys Ile Lys Asn
                325                 330                 335

Lys Pro Ile Val Asn Ile Asp Pro Gln Thr Ala Glu Leu Asn His Leu
            340                 345                 350

Lys Gln Gln Val Gln Gln Leu Gln Val Leu Leu Leu Gln Ala His Gly
        355                 360                 365

Gly Thr Leu Pro Gly Ser Ile Thr Val Glu Pro Ser Glu Asn Leu Gln
    370                 375                 380

Ser Leu Met Glu Lys Asn Gln Ser Leu Val Glu Glu Asn Glu Lys Leu
385                 390                 395                 400

Ser Arg Gly Leu Ser Glu Ala Ala Gly Gln Thr Ala Gln Met Leu Glu
                405                 410                 415

Arg Ile Ile Trp Thr Glu Gln Ala Asn Glu Lys Met Asn Ala Lys Leu
            420                 425                 430

Glu Glu Leu Arg Gln His Ala Ala Cys Lys Leu Asp Leu Gln Lys Leu
        435                 440                 445

Val Glu Thr Leu Glu Asp Gln Glu Leu Lys Glu Asn Val Glu Ile Ile
    450                 455                 460

Cys Asn Leu Gln Gln Leu Ile Thr Gln
465                 470

<210> SEQ ID NO 7
<211> LENGTH: 4127
<212> TYPE: DNA
<213> ORGANISM: Human
```

<400> SEQUENCE: 7

```
tttgaaactt ggcggttaaa gctccggctg ggcaggggcg gcgggagacc ccggggtgaac      60
ggggaaggga catttagttt gagacggtgc tgagatagga tcatgaagga agaggtgaag     120
ggaattcctg taagagtggc actgcgttgt cgccctctgg tccccaaaga gattagcgag     180
ggctgccaga tgtgcctttc cttcgtgccc ggggagactc aggtggtggt tggtactgat     240
aaatccttca cctacgattt tgtgtttgac ccctgtactg agcaggaaga agtcttcaat     300
aaagcagtag cgccgctcat aaaaggcata tttaaaggat ataatgcaac ggtcctggcc     360
tatgggcaga ctggctctgg aaaaacctat tcaatgggag gtgcatacac tgcggagcag     420
gagaatgaac aacagttgg cattattcct agggtaatac aactgctctt caaagaaatt     480
gatcaaaaga gtgactttga atttactctg aaagtgtctt acttagagat ttacaatgaa     540
gaattttgg atcttctatg cccatctcgt gagaaagctc aaataaatat acgggaggat     600
cctaaggaag gcataaagat tgtgggactc actgagaaga ctgttttagt tgccttggat     660
actgtttcct gtttggagca gggcaacaac tctaggactg tggcctccac agctatgaac     720
tcccagtcgt cccgatctca tgccatctttt acaatctcct tagagcaagg aaagaaaagt     780
gacaagaata gcagctttcg ctccaagctg catcttgtag acctcgctgg atcagaaaga     840
cagaagaaaa ccaaggctga aggggatcgt ctaaagagg gtattaatat taaccgaggc     900
ctcctatgct tgggaaatgt aatcagtgct cttggagatg acaaaaaggg tagctttgtg     960
ccctacagag attccaagtt aactcgactg ctgcaagatt ctctaggagg taacagccac    1020
actcttatga tagcctgtgt gagtcctgct gactccaatc tagaggaaac attaagtacc    1080
cttcgctatg ctgacagagc aagaaaaatc aagaacaaac ctattgttaa tattgatccc    1140
cacacagctg aacttaatca tctaaagcaa caggtacaac agctacaagt cttgttgcta    1200
caagcccatg gaggtacccct gcctggatct ataaatgcag aaccatcaga gaatctacaa    1260
tccctgatgg agaagaatca gtccctggta gaggagaatg aaaaattaag tcgttgtctg    1320
agcaaggcag ctggtcagac agcccagatg ttggagagga tcattttgac agagcaagtg    1380
aatgaaaaac tgaacgccaa gctagaagag ctcaggcagc atgcggcctg caagctggat    1440
cttcaaaagc tagtggagac tttggaagac caggaattga agaaaatgt agagataatt    1500
tgtaacctgc agcaactgat tacccagtta tcagatgaaa ctgttgcttg cacggctgca    1560
gccattgata ctgcggtaga agaagaagct caagtggaaa ccagtccaga gacaagcagg    1620
tcttctgacg cttttaccac tcagcatgct ctccatcaag ctcagatgtc taaggaggtg    1680
gttgagttga ataacgccct tgcactgaaa gaggccctag ttaggaagat gactcagaac    1740
gacaaccaac tacagcccat tcagtttcaa taccaggata acataaaaaa tctagaatta    1800
gaagtcatca atctgcaaaa ggaaaaggaa gaattggttc gtgaacttca gacagcaaag    1860
aagaatgcca accaagccaa gctgagtgag caccgtcgca aacttctcca ggagctggag    1920
ggtcaaatag ctgatctgaa gaagaaactg aatgagcagt ccaaacttct gaaactaaag    1980
gaatccacag agcgtactgt ctccaaactg aaccaggaga tacggatgat gaaaaaccag    2040
cgggtacagt taatgcgtca aatgaaagag gatgctgaga agtttagaca gtggaagcag    2100
aaaagagaca agaagtaat acagttaaaa gaacgagacc gtaagaggca atatgagctg    2160
ctgaaacttg aaagaaactt ccagaaacaa tccaatgtgc tcagacgtaa aacgaggag    2220
gcagcagctg ccaacaagcg tctcaaggat gctctccaga acaacggga ggttgcagat    2280
```

-continued

```
aagcggaaag agactcagag ccgtggaatg gaaggcactg cagctcgagt gaggaattgg    2340
cttggaaatg aaattgaggt tatggtcagt actgaggaag ccaaacgcca tctgaatgac    2400
ctccttgaag acagaaagat cctggctcag gatgtggttc aactcaaaga aaaaaggaa     2460 tctcgggaga atccacctcc taaactccgg aagtgtacat tctccctttc tgaggtgcat    2520
ggtcaagttt tggagtcaga agattgtatt acaaaacaga ttgaaagcct agagactgaa    2580
atggaactca ggagtgctca gattgctgac ctacagcaga agctgctgga tgcagaaagt    2640
gaagataggc gbcaaaacaa tgctgggaga atattgccac cattctggaa gccaagtgtg    2700
ccctgaaata tttgattgga gagctggtct cctccaaaat acatgtcacc aaacttgaaa    2760
acagcctgag acagagcaag gccagctgtg ctgacatgca aagatgcta tttgaggaac     2820 aaaatcattt ttctgagata gagacagagt tacaagctga gctggtcaga atggagcaac    2880
agcaccaaga gaaggtgcta taccttgtca gccagctgca ggaaagccaa atggcagaga    2940
agcagttaga gaaatcagcc agtgaaaagg aaccacagtt ggtgagcaca ctgcagtgtc    3000
aggatgaaga acttgagaag atgcgagaag tgtgtgagca aaatcagcag cttctccaag    3060
agaatgaaat catcaagcag aaactgatcc tcctccaggt agccagcaga cagaaacatc    3120
ttcctaatga taccttcta tctccagact cttcttttga atatatccca cctaagccaa     3180
aaccttctcg tgttaaagaa aagtttctgg agcaaagcat ggacatcgag gatctaaaat    3240
attgttcaga gcattctgtg aatgagcatg aagatggtga tggtgatggc gacagtgatg    3300
agggggatga tgaggaatgg aagccaacaa aattagtcaa ggtgtccagg aagaacatcc    3360
aagggtgttc ctgcaagggc tggtgtggga caagcagtg tgggtgcagg aagcaaaagt      3420
cagactgtgg tgtggactgt agctgtgacc ccacaaagtg tcggaaccgc cagcaaggca    3480
aggatagctt gggcactgtt gaacagaccc aggattccga aggctccttc aaactggagg    3540
atcctaccga ggtgaccca ggattgagct tctttaaccc tgtctgtgcc accccaata     3600 gcaagatcct gaaagagatg tgtgacatgg agcaggtgct gtcaaagaag actgctccag    3660
ctccctcccc ttttgacctc ccagagtcga acatggagc aacagaatac caacaaaata     3720
agcctccagg gaagaaaaag aaacgagctc tggctagcaa caccagcttc ttctctggct    3780
gctcccctat tgaagaagag gcccactgaa gttggagtca tcatctctac ccccaatctg    3840
gcttgggaga tgcttttccag ttgcagccag aagggggtttt ttaaatgact tctctggatt    3900
tcaggtttct tgccgttgaa aaaaaggaac aaagcattac taaaaagaag gtaacctttg    3960
ttggatgttg tccctcagtc tccatcccca gactactgct ctctgctctc tagaaggctg    4020
ctaaaccacc tgctgaagag agaaccaaca gactttccta atgactactc aggaaccagt    4080
cctcagtatg atcaagttcc ttcttatttg tgagcagttc aggctat                  4127
```

<210> SEQ ID NO 8
<211> LENGTH: 1234
<212> TYPE: PRT
<213> ORGANISM: Human

<400> SEQUENCE: 8

```
Met Lys Glu Glu Val Lys Gly Ile Pro Val Arg Val Ala Leu Arg Cys
 1               5                  10                  15

Arg Pro Leu Val Pro Lys Glu Ile Ser Glu Gly Cys Gln Met Cys Leu
            20                  25                  30

Ser Phe Val Pro Gly Glu Thr Gln Val Val Gly Thr Asp Lys Ser
         35                  40                  45
```

-continued

```
Phe Thr Tyr Asp Phe Val Phe Asp Pro Cys Thr Glu Gln Glu Glu Val
 50                  55                  60
Phe Asn Lys Ala Val Ala Pro Leu Ile Lys Gly Ile Phe Lys Gly Tyr
 65                  70                  75                  80
Asn Ala Thr Val Leu Ala Tyr Gly Gln Thr Gly Ser Gly Lys Thr Tyr
                     85                  90                  95
Ser Met Gly Gly Ala Tyr Thr Ala Glu Gln Glu Asn Glu Pro Thr Val
                    100                 105                 110
Gly Ile Ile Pro Arg Val Ile Gln Leu Leu Phe Lys Glu Ile Asp Gln
                115                 120                 125
Lys Ser Asp Phe Glu Phe Thr Leu Lys Val Ser Tyr Leu Glu Ile Tyr
            130                 135                 140
Asn Glu Glu Ile Leu Asp Leu Leu Cys Pro Ser Arg Glu Lys Ala Gln
145                 150                 155                 160
Ile Asn Ile Arg Glu Asp Pro Lys Glu Gly Ile Lys Ile Val Gly Leu
                165                 170                 175
Thr Glu Lys Thr Val Leu Val Ala Leu Asp Thr Val Ser Cys Leu Glu
                180                 185                 190
Gln Gly Asn Asn Ser Arg Thr Val Ala Ser Thr Ala Met Asn Ser Gln
                195                 200                 205
Ser Ser Arg Ser His Ala Ile Phe Thr Ile Ser Leu Glu Gln Gly Lys
210                 215                 220
Lys Ser Asp Lys Asn Ser Ser Phe Arg Ser Lys Leu His Leu Val Asp
225                 230                 235                 240
Leu Ala Gly Ser Glu Arg Gln Lys Lys Thr Lys Ala Glu Gly Asp Arg
                245                 250                 255
Leu Lys Glu Gly Ile Asn Ile Asn Arg Gly Leu Leu Cys Leu Gly Asn
                260                 265                 270
Val Ile Ser Ala Leu Gly Asp Asp Lys Lys Gly Ser Phe Val Pro Tyr
                275                 280                 285
Arg Asp Ser Lys Leu Thr Arg Leu Leu Gln Asp Ser Leu Gly Gly Asn
290                 295                 300
Ser His Thr Leu Met Ile Ala Cys Val Ser Pro Ala Asp Ser Asn Leu
305                 310                 315                 320
Glu Glu Thr Leu Ser Thr Leu Arg Tyr Ala Asp Arg Ala Arg Lys Ile
                325                 330                 335
Lys Asn Lys Pro Ile Val Asn Ile Asp Pro His Thr Ala Glu Leu Asn
                340                 345                 350
His Leu Lys Gln Gln Val Gln Gln Leu Gln Val Leu Leu Leu Gln Ala
            355                 360                 365
His Gly Gly Thr Leu Pro Gly Ser Ile Asn Ala Glu Pro Ser Glu Asn
            370                 375                 380
Leu Gln Ser Leu Met Glu Lys Asn Gln Ser Leu Val Glu Glu Asn Glu
385                 390                 395                 400
Lys Leu Ser Arg Cys Leu Ser Lys Ala Ala Gly Gln Thr Ala Gln Met
                405                 410                 415
Leu Glu Arg Ile Ile Leu Thr Glu Gln Val Asn Glu Lys Leu Asn Ala
                420                 425                 430
Lys Leu Glu Glu Leu Arg Gln His Ala Ala Cys Lys Leu Asp Leu Gln
            435                 440                 445
Lys Leu Val Glu Thr Leu Glu Asp Gln Glu Leu Lys Glu Asn Val Glu
450                 455                 460
Ile Ile Cys Asn Leu Gln Gln Leu Ile Thr Gln Leu Ser Asp Glu Thr
```

-continued

```
465                 470                 475                 480

Val Ala Cys Thr Ala Ala Ile Asp Thr Ala Val Glu Glu Ala
                485                 490                 495

Gln Val Glu Thr Ser Pro Glu Thr Ser Arg Ser Ser Asp Ala Phe Thr
                500                 505                 510

Thr Gln His Ala Leu His Gln Ala Gln Met Ser Lys Glu Val Val Glu
                515                 520                 525

Leu Asn Asn Ala Leu Ala Leu Lys Glu Ala Leu Val Arg Lys Met Thr
            530                 535                 540

Gln Asn Asp Asn Gln Leu Gln Pro Ile Gln Phe Gln Tyr Gln Asp Asn
545                 550                 555                 560

Ile Lys Asn Leu Glu Leu Glu Val Ile Asn Leu Gln Lys Glu Lys Glu
                565                 570                 575

Glu Leu Val Arg Glu Leu Gln Thr Ala Lys Lys Asn Ala Asn Gln Ala
                580                 585                 590

Lys Leu Ser Glu His Arg Arg Lys Leu Leu Gln Glu Leu Glu Gly Gln
                595                 600                 605

Ile Ala Asp Leu Lys Lys Lys Leu Asn Glu Gln Ser Lys Leu Leu Lys
        610                 615                 620

Leu Lys Glu Ser Thr Glu Arg Thr Val Ser Lys Leu Asn Gln Glu Ile
625                 630                 635                 640

Arg Met Met Lys Asn Gln Arg Val Gln Leu Met Arg Gln Met Lys Glu
                645                 650                 655

Asp Ala Glu Lys Phe Arg Gln Trp Lys Gln Lys Arg Asp Lys Glu Val
                660                 665                 670

Ile Gln Leu Lys Glu Arg Asp Arg Lys Arg Gln Tyr Glu Leu Leu Lys
            675                 680                 685

Leu Glu Arg Asn Phe Gln Lys Gln Ser Asn Val Leu Arg Arg Lys Thr
        690                 695                 700

Glu Glu Ala Ala Ala Ala Asn Lys Arg Leu Lys Asp Ala Leu Gln Lys
705                 710                 715                 720

Gln Arg Glu Val Ala Asp Lys Arg Lys Glu Thr Gln Ser Arg Gly Met
                725                 730                 735

Glu Gly Thr Ala Ala Arg Val Arg Asn Trp Leu Gly Asn Glu Ile Glu
                740                 745                 750

Val Met Val Ser Thr Glu Glu Ala Lys Arg His Leu Asn Asp Leu Leu
                755                 760                 765

Glu Asp Arg Lys Ile Leu Ala Gln Asp Val Val Gln Leu Lys Glu Lys
        770                 775                 780

Lys Glu Ser Arg Glu Asn Pro Pro Lys Leu Arg Lys Cys Thr Phe
785                 790                 795                 800

Ser Leu Ser Glu Val His Gly Gln Val Leu Glu Ser Glu Asp Cys Ile
                805                 810                 815

Thr Lys Gln Ile Glu Ser Leu Glu Thr Glu Met Glu Leu Arg Ser Ala
            820                 825                 830

Gln Ile Ala Asp Leu Gln Gln Lys Leu Leu Asp Ala Glu Ser Glu Asp
        835                 840                 845

Arg Pro Lys Gln Cys Trp Glu Asn Ile Ala Thr Ile Leu Glu Ala Lys
    850                 855                 860

Cys Ala Leu Lys Tyr Leu Ile Gly Glu Leu Val Ser Ser Lys Ile His
865                 870                 875                 880

Val Thr Lys Leu Glu Asn Ser Leu Arg Gln Ser Lys Ala Ser Cys Ala
                885                 890                 895
```

```
Asp Met Gln Lys Met Leu Phe Glu Glu Gln Asn His Phe Ser Glu Ile
            900                 905                 910

Glu Thr Glu Leu Gln Ala Glu Leu Val Arg Met Glu Gln Gln His Gln
        915                 920                 925

Glu Lys Val Leu Tyr Leu Val Ser Gln Leu Gln Glu Ser Gln Met Ala
        930                 935                 940

Glu Lys Gln Leu Glu Lys Ser Ala Ser Glu Lys Glu Pro Gln Leu Val
945                 950                 955                 960

Ser Thr Leu Gln Cys Gln Asp Glu Glu Leu Glu Lys Met Arg Glu Val
                965                 970                 975

Cys Glu Gln Asn Gln Gln Leu Leu Gln Glu Asn Glu Ile Ile Lys Gln
            980                 985                 990

Lys Leu Ile Leu Leu Gln Val Ala Ser Arg Gln Lys His Leu Pro Asn
            995                 1000                1005

Asp Thr Leu Leu Ser Pro Asp Ser Ser Phe Glu Tyr Ile Pro Pro Lys
        1010                1015                1020

Pro Lys Pro Ser Arg Val Lys Glu Lys Phe Leu Glu Gln Ser Met Asp
1025                1030                1035                1040

Ile Glu Asp Leu Lys Tyr Cys Ser Glu His Ser Val Asn Glu His Glu
            1045                1050                1055

Asp Gly Asp Gly Asp Gly Asp Ser Asp Glu Gly Asp Asp Glu Glu Trp
            1060                1065                1070

Lys Pro Thr Lys Leu Val Lys Val Ser Arg Lys Asn Ile Gln Gly Cys
            1075                1080                1085

Ser Cys Lys Gly Trp Cys Gly Asn Lys Gln Cys Gly Cys Arg Lys Gln
    1090                1095                1100

Lys Ser Asp Cys Gly Val Asp Cys Ser Cys Asp Pro Thr Lys Cys Arg
1105                1110                1115                1120

Asn Arg Gln Gln Gly Lys Asp Ser Leu Gly Thr Val Glu Gln Thr Gln
                1125                1130                1135

Asp Ser Glu Gly Ser Phe Lys Leu Glu Asp Pro Thr Glu Val Thr Pro
            1140                1145                1150

Gly Leu Ser Phe Phe Asn Pro Val Cys Ala Thr Pro Asn Ser Lys Ile
            1155                1160                1165

Leu Lys Glu Met Cys Asp Met Glu Gln Val Leu Ser Lys Lys Thr Ala
    1170                1175                1180

Pro Ala Pro Ser Pro Phe Asp Leu Pro Glu Ser Lys His Gly Ala Thr
1185                1190                1195                1200

Glu Tyr Gln Gln Asn Lys Pro Pro Gly Lys Lys Lys Arg Ala Leu
                1205                1210                1215

Ala Ser Asn Thr Ser Phe Phe Ser Gly Cys Ser Pro Ile Glu Glu Glu
            1220                1225                1230

Ala His
```